(12) United States Patent
Padget et al.

(10) Patent No.: US 7,670,284 B2
(45) Date of Patent: Mar. 2, 2010

(54) MEDICAL DEVICE WITH ARTICULATING SHAFT

(75) Inventors: Martin Padget, Valencia, CA (US); David Skinlo, Logan, UT (US); Thomas Weisel, Ventura, CA (US); Longo Chu, Newhall, CA (US); Roger Pisarnwongs, Sylmar, CA (US)

(73) Assignee: Surgical Solutions LLC, Valencia, CA (US)

( * ) Notice: Subject to any disclaimer, the term of this patent is extended or adjusted under 35 U.S.C. 154(b) by 0 days.

(21) Appl. No.: 11/760,475

(22) Filed: Jun. 8, 2007

(65) Prior Publication Data

US 2008/0221393 A1 Sep. 11, 2008

Related U.S. Application Data

(63) Continuation-in-part of application No. 11/211,834, filed on Aug. 25, 2005, now Pat. No. 7,553,275.

(60) Provisional application No. 60/804,184, filed on Jun. 8, 2006, provisional application No. 60/676,456, filed on Apr. 28, 2005, provisional application No. 60/646,966, filed on Jan. 24, 2005, provisional application No. 60/606,245, filed on Aug. 31, 2004.

(51) Int. Cl.
*A61B 1/00* (2006.01)
(52) U.S. Cl. .................. 600/142; 600/141; 600/146
(58) Field of Classification Search ............... 606/1; 600/139–142, 146–150, 101, 128, 130
See application file for complete search history.

(56) References Cited

U.S. PATENT DOCUMENTS

| | | | |
|---|---|---|---|
| 2,028,635 A | 1/1936 | Wappler | |
| 3,190,286 A * | 6/1965 | Stokes | ............ 600/141 |
| 3,314,431 A | 4/1967 | Smith, Jr. | |
| 3,470,876 A | 10/1969 | Barchilon | |
| 3,605,725 A | 9/1971 | Bentor | |
| 3,788,303 A | 1/1974 | Hall | |
| 4,483,562 A | 11/1984 | Schoolman | |
| 4,662,371 A | 5/1987 | Whipple | |
| 4,672,964 A | 6/1987 | Dee | |
| 4,763,669 A | 8/1988 | Jaeger | |
| 4,790,294 A | 12/1988 | Allred, III et al. | |
| 4,834,069 A | 5/1989 | Umeda | |
| 4,880,015 A | 11/1989 | Nierman | |

(Continued)

FOREIGN PATENT DOCUMENTS

DE 3920706 6/1989

(Continued)

*Primary Examiner*—John P Leubecker
*Assistant Examiner*—Victoria W Chen
(74) *Attorney, Agent, or Firm*—Myers Andras Sherman LLP; Joseph C. Andras

(57) ABSTRACT

A medical device (10) includes an articulating shaft (20, 20a, 20b, 20c, 20d, 20e, or 20f) with a pair of slat assemblies (31, 33). By moving an articulator (37), the slat assemblies (31, 33) are configured to concurrently push while the other pulls in order to bend the articulating shaft (20). The articulating shaft (20) includes a series of pivot members (26, 26a, 26b, 26c, 26d, 126e and 226e, or 126f and 226f). The pivot members (26) may include inner links (126e, 126f) and outer links (226e, 226f). A method for articulating a shaft of a medical device is also provided.

24 Claims, 23 Drawing Sheets

U.S. PATENT DOCUMENTS

| | | | |
|---|---|---|---|
| 4,934,340 A | 6/1990 | Ebling et al. |
| 4,945,920 A | 8/1990 | Clossick |
| 5,025,804 A | 6/1991 | Kondo |
| 5,042,707 A | 8/1991 | Taheri |
| 5,067,957 A | 11/1991 | Jervis |
| 5,143,475 A | 9/1992 | Chikama |
| 5,171,314 A | 12/1992 | Dulebohn |
| 5,178,129 A | 1/1993 | Chikama |
| 5,195,968 A | 3/1993 | Lundquist |
| 5,201,741 A | 4/1993 | Dulebohn |
| 5,209,747 A | 5/1993 | Knoepfler |
| 5,254,130 A | 10/1993 | Poncet |
| 5,284,128 A | 2/1994 | Hart |
| 5,289,963 A | 3/1994 | McGarry |
| 5,300,087 A | 4/1994 | Knoepfler |
| 5,308,324 A | 5/1994 | Hammerslag |
| 5,318,528 A | 6/1994 | Heaven |
| 5,330,502 A | 7/1994 | Hassler |
| 5,352,237 A | 10/1994 | Rodak |
| 5,403,342 A | 4/1995 | Tovey |
| 5,405,344 A | 4/1995 | Williamson |
| 5,417,203 A | 5/1995 | Tovey |
| 5,431,323 A | 7/1995 | Smith |
| 5,450,842 A | 9/1995 | Tovey |
| 5,454,827 A | 10/1995 | Aust |
| 5,468,250 A | 11/1995 | Paraschac |
| 5,478,003 A | 12/1995 | Green |
| 5,480,382 A | 1/1996 | Hammerslag |
| 5,484,095 A | 1/1996 | Green |
| 5,487,757 A | 1/1996 | Truckai |
| 5,497,933 A | 3/1996 | DeFonzo |
| 5,501,654 A | 3/1996 | Failla |
| 5,507,773 A | 4/1996 | Huitema |
| 5,520,678 A | 5/1996 | Heckele |
| 5,531,686 A | 7/1996 | Lundquist |
| 5,535,754 A | 7/1996 | Doherty |
| 5,540,706 A | 7/1996 | Aust |
| 5,549,637 A | 8/1996 | Crainich |
| 5,562,682 A | 10/1996 | Oberlin |
| 5,569,270 A | 10/1996 | Weng |
| 5,582,617 A | 12/1996 | Klieman |
| 5,588,964 A | 12/1996 | Imran et al. |
| 5,609,601 A | 3/1997 | Kolesa |
| 5,618,294 A | 4/1997 | Aust |
| 5,620,415 A | 4/1997 | Lucey |
| 5,620,447 A | 4/1997 | Smith |
| 5,632,432 A | 5/1997 | Schulze |
| 5,643,294 A | 7/1997 | Tovey |
| 5,645,075 A | 7/1997 | Palmer |
| 5,649,955 A | 7/1997 | Hashimoto |
| 5,662,662 A | 9/1997 | Bishop |
| 5,669,544 A | 9/1997 | Schulze |
| 5,669,926 A | 9/1997 | Aust |
| 5,673,840 A | 10/1997 | Schulze |
| 5,673,841 A | 10/1997 | Schulze |
| 5,680,982 A | 10/1997 | Schulze |
| 5,692,668 A | 12/1997 | Schulze |
| 5,702,408 A | 12/1997 | Wales |
| 5,704,534 A | 1/1998 | Huitema |
| 5,713,505 A | 2/1998 | Huitema |
| 5,725,536 A | 3/1998 | Oberlin |
| 5,752,973 A | 5/1998 | Kieturakis |
| 5,766,196 A | 6/1998 | Griffiths |
| 5,766,205 A | 6/1998 | Zvenyatsky |
| 5,782,828 A | 7/1998 | Chen et al. |
| 5,782,859 A | 7/1998 | Nicholas |
| 5,797,537 A | 8/1998 | Oberlin |
| 5,810,716 A | 9/1998 | Mukherjee |
| 5,820,009 A | 10/1998 | Melling |
| 5,823,066 A | 10/1998 | Huitema et al. |
| 5,833,692 A | 11/1998 | Cesarini |
| 5,840,043 A | 11/1998 | Palmer |
| 5,851,212 A | 12/1998 | Zirps |
| 5,857,964 A | 1/1999 | Konstorum |
| 5,860,995 A | 1/1999 | Berkelaar |
| 5,885,288 A | 3/1999 | Aust |
| 5,899,914 A | 5/1999 | Zirps |
| 5,916,147 A * | 6/1999 | Boury ..................... 600/146 |
| 5,919,199 A | 7/1999 | Mers Kelly et al. |
| 5,938,678 A | 8/1999 | Zirps |
| 5,967,997 A | 10/1999 | Turturro |
| 6,033,378 A | 3/2000 | Lundquist |
| 6,048,339 A | 4/2000 | Zirps |
| 6,051,010 A | 4/2000 | DiMatteo |
| 6,053,907 A | 4/2000 | Zirps |
| 6,063,098 A | 5/2000 | Houser |
| 6,068,648 A | 5/2000 | Cole |
| 6,077,287 A | 6/2000 | Taylor |
| 6,319,195 B1 | 11/2001 | Nakaichi |
| 6,408,889 B1 * | 6/2002 | Komachi ................. 138/120 |
| 6,464,703 B2 | 10/2002 | Bartel |
| 6,491,626 B1 | 12/2002 | Matsuura et al. |
| 6,554,844 B2 | 4/2003 | Lee |
| 6,569,105 B1 | 5/2003 | Kortenbach |
| 6,585,718 B2 | 7/2003 | Hayzelden |
| 6,607,496 B1 | 8/2003 | Poor |
| RE38,335 E | 11/2003 | Aust et al. |
| 6,645,218 B1 | 11/2003 | Cassidy |
| 6,666,854 B1 | 12/2003 | Lange |
| 6,702,780 B1 | 3/2004 | Gilboa et al. |
| 6,716,207 B2 | 4/2004 | Farnholtz |
| 6,743,239 B1 | 6/2004 | Kuehn |
| 6,743,240 B2 | 6/2004 | Smith |
| 6,802,840 B2 | 10/2004 | Chin |
| 6,824,548 B2 | 11/2004 | Smith |
| 6,863,668 B2 | 3/2005 | Gillespie |
| 6,869,414 B2 | 3/2005 | Simpson |
| 6,877,647 B2 | 4/2005 | Green |
| 6,921,408 B2 | 7/2005 | Sauer |
| 7,041,052 B2 * | 5/2006 | Saadat et al. ............. 600/114 |
| 2003/0032970 A1 | 2/2003 | Hitlebrandt |
| 2003/0083550 A1 * | 5/2003 | Miyagi .................... 600/141 |
| 2004/0122449 A1 | 6/2004 | Modesitt et al. |
| 2004/0167547 A1 | 8/2004 | Beane et al. |
| 2004/0236316 A1 | 11/2004 | Danitz et al. |
| 2005/0006430 A1 | 1/2005 | Wales |

FOREIGN PATENT DOCUMENTS

| | | |
|---|---|---|
| DE | 4136861 | 11/1991 |
| DE | 4204051 | 2/1992 |
| EP | 0301288 | 7/1988 |
| FR | 2662778 | 5/1990 |
| WO | WO9300048 | 6/1991 |
| WO | WO9304634 | 3/1993 |
| WO | WO9320760 | 4/1993 |

* cited by examiner

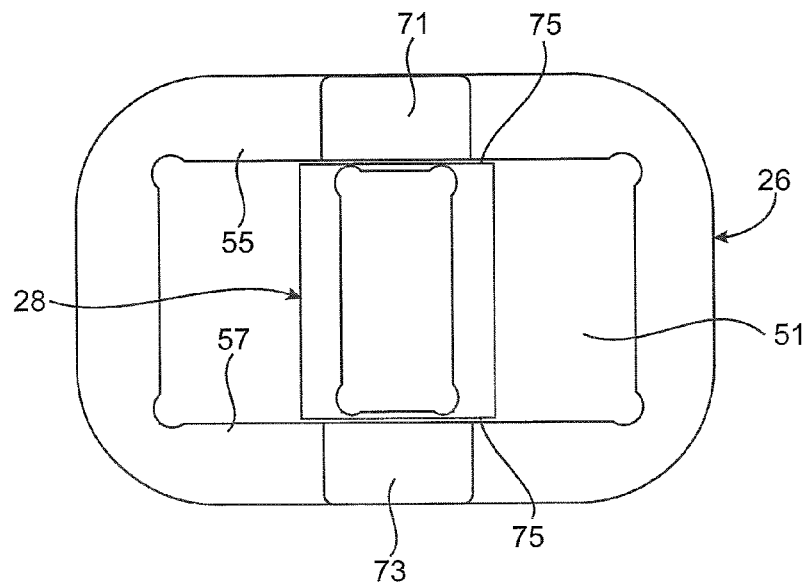
FIG. 6
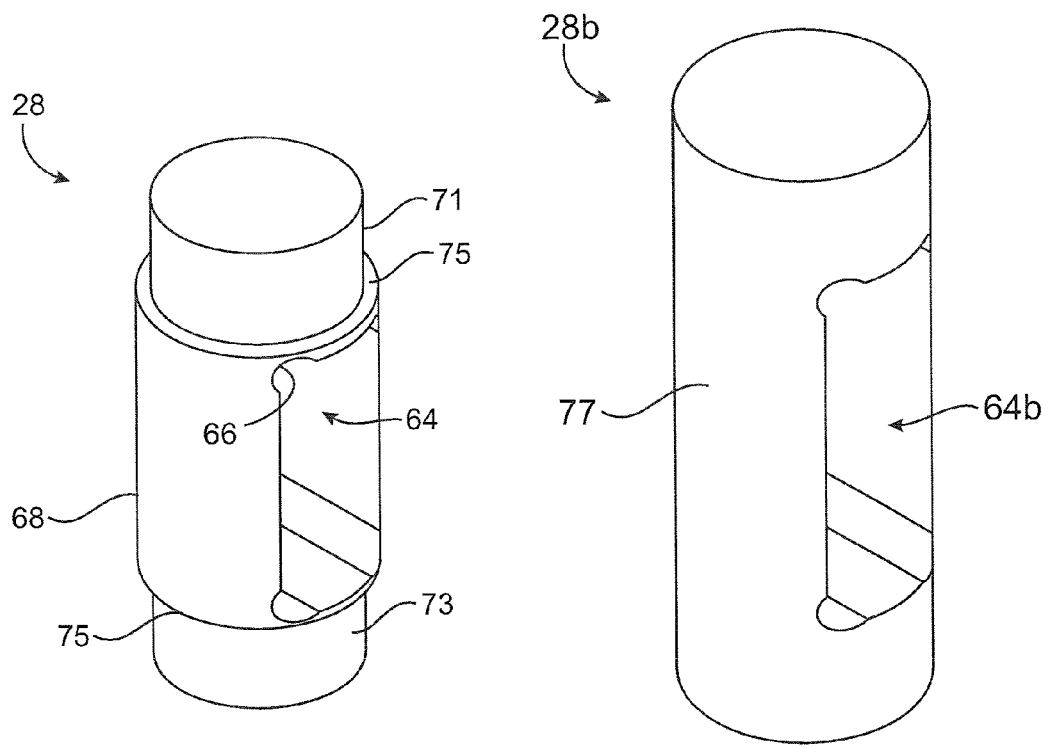
FIG. 5
FIG. 7

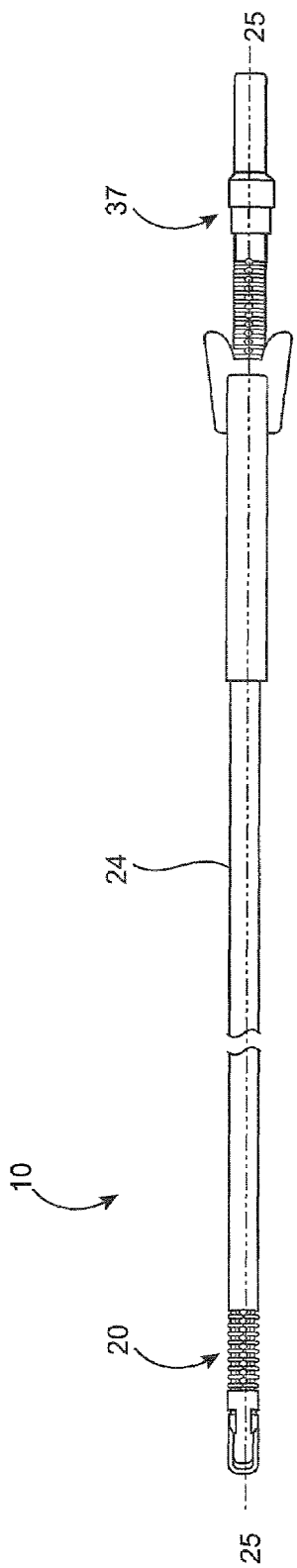
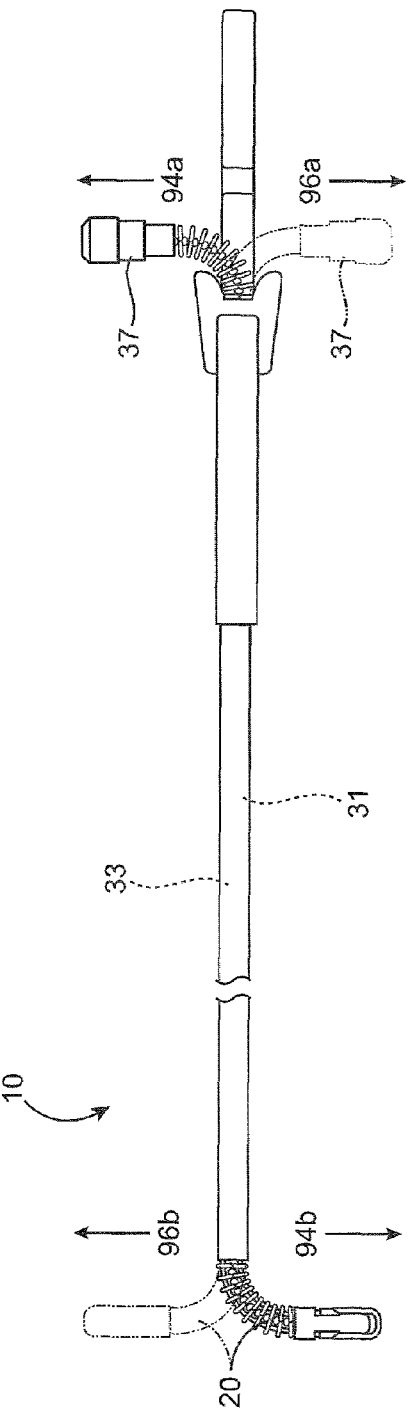
FIG. 10
FIG. 11

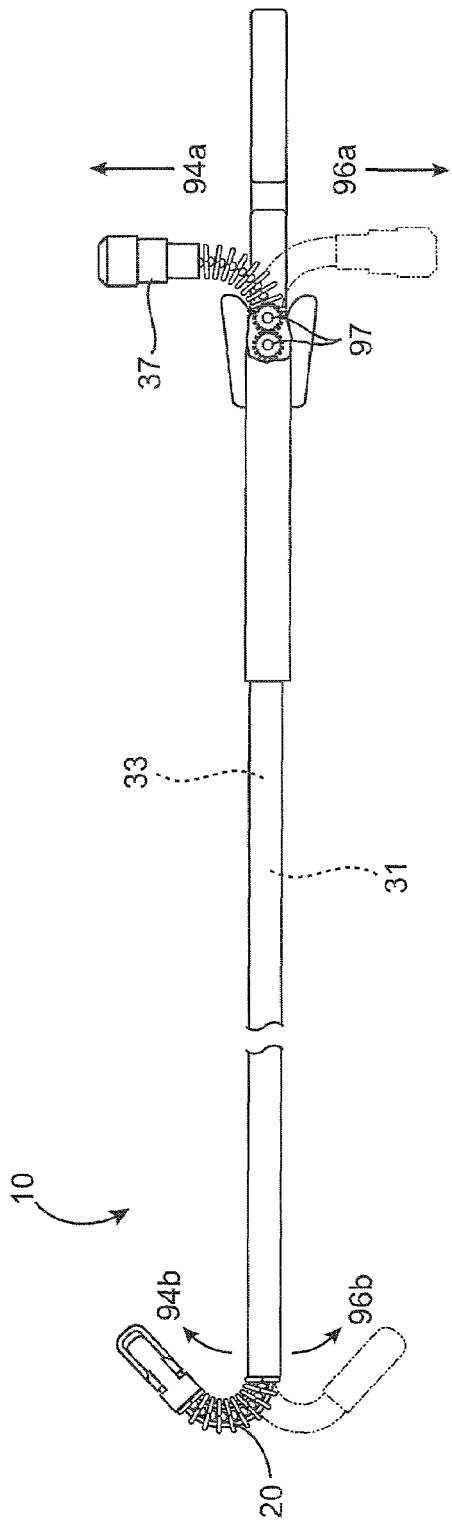
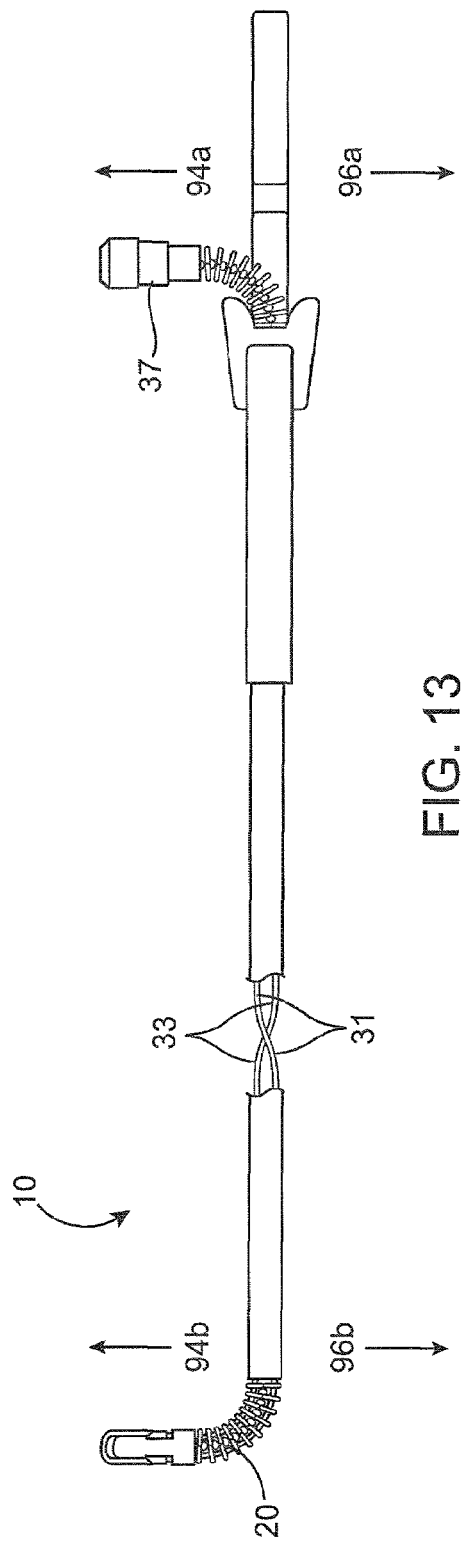
FIG. 12
FIG. 13

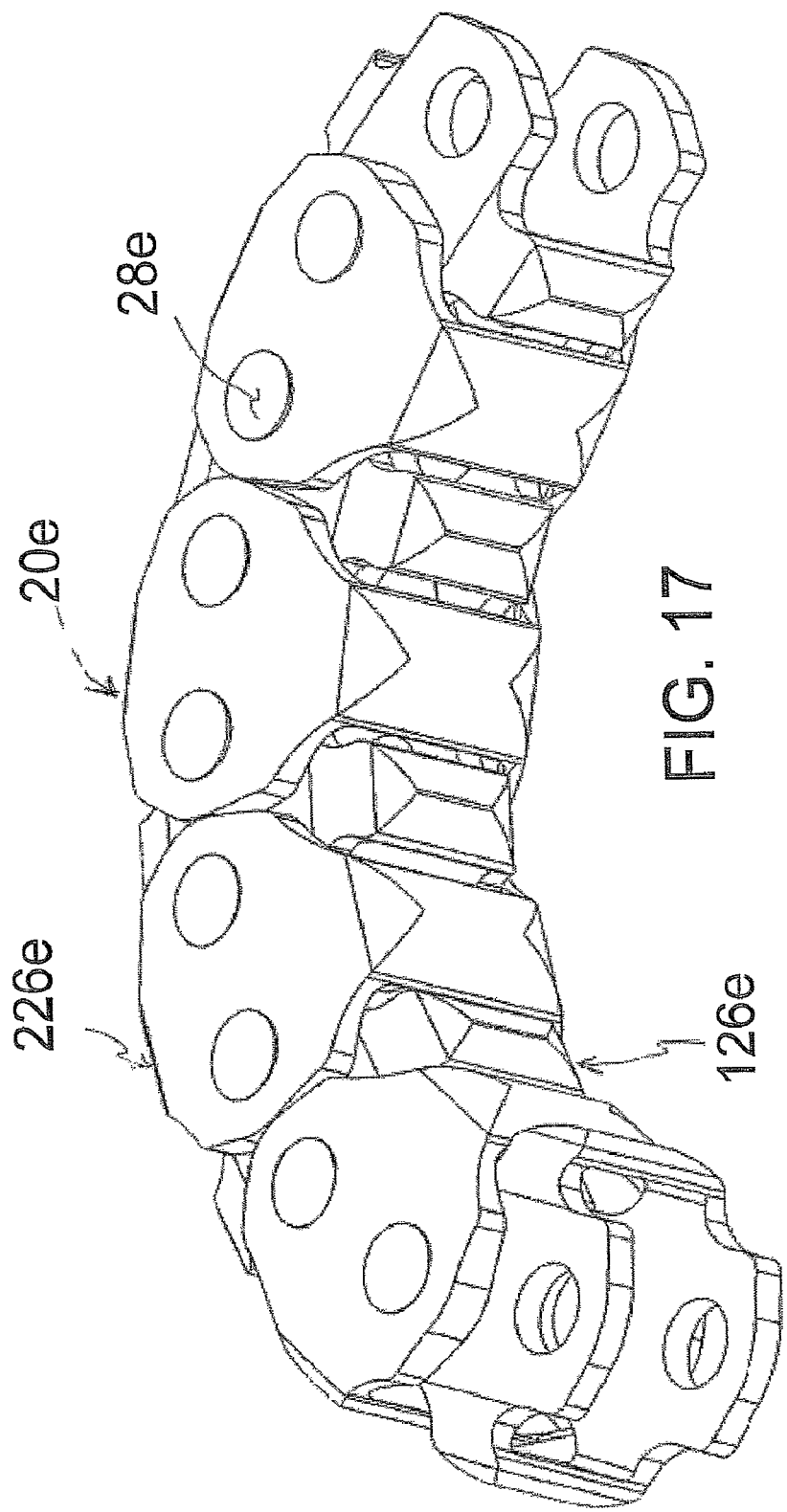

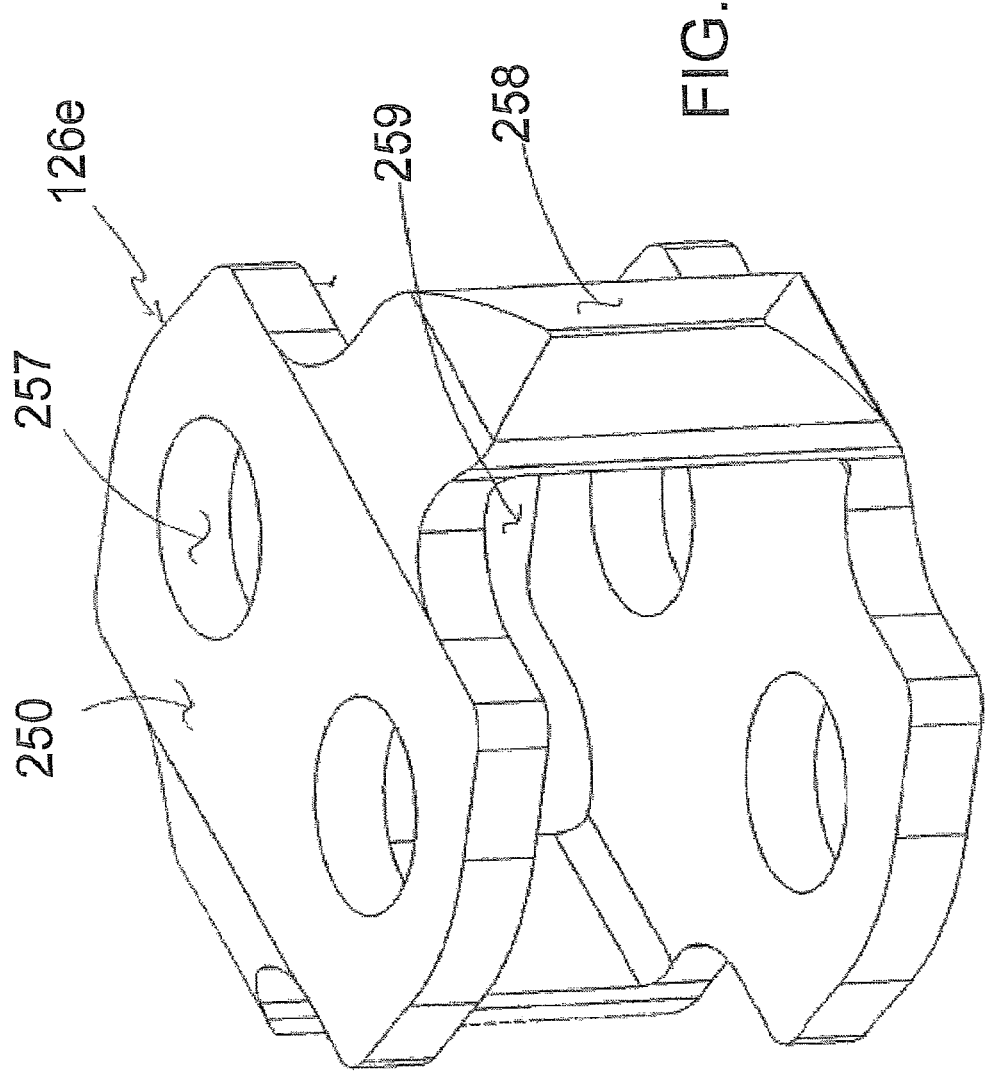

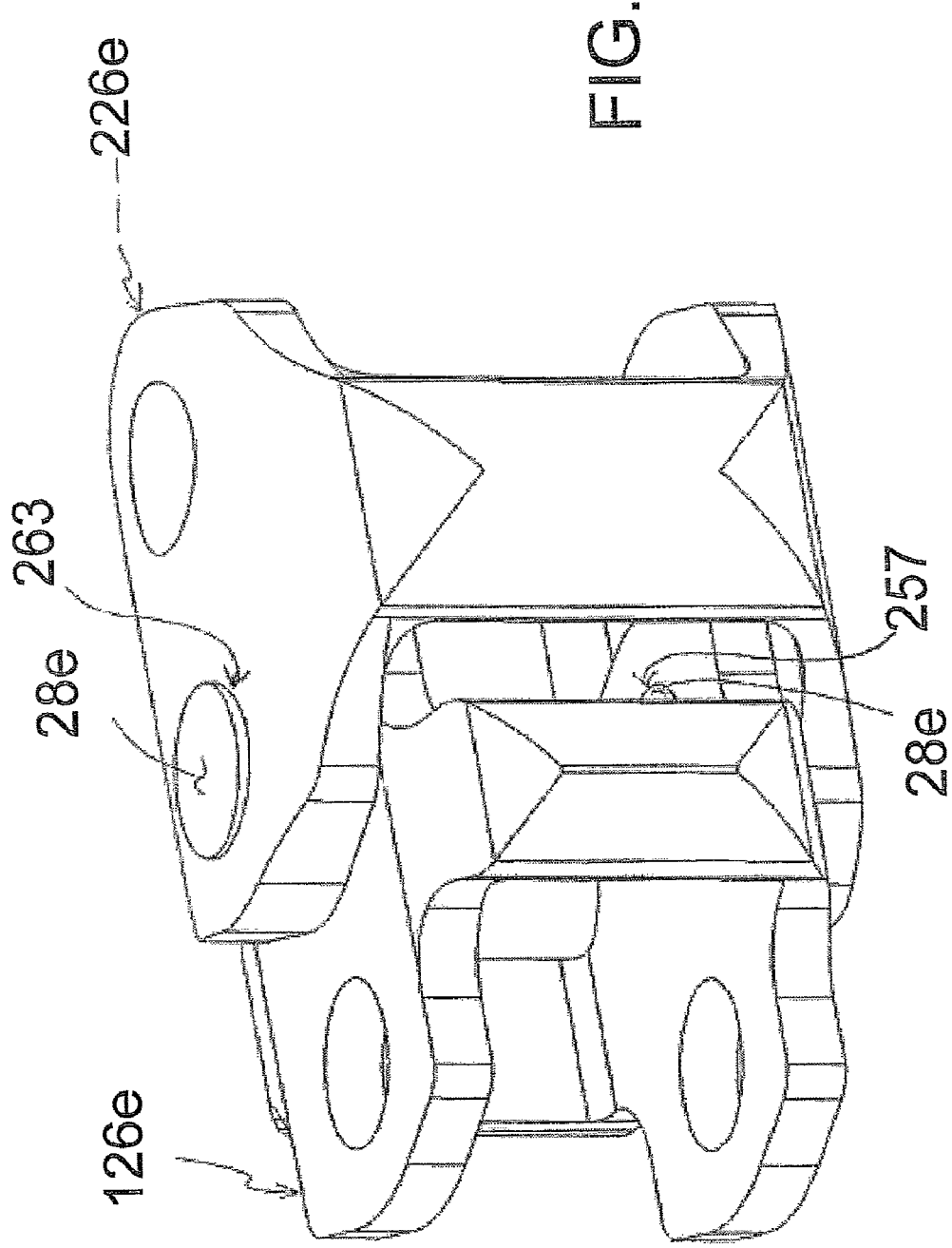

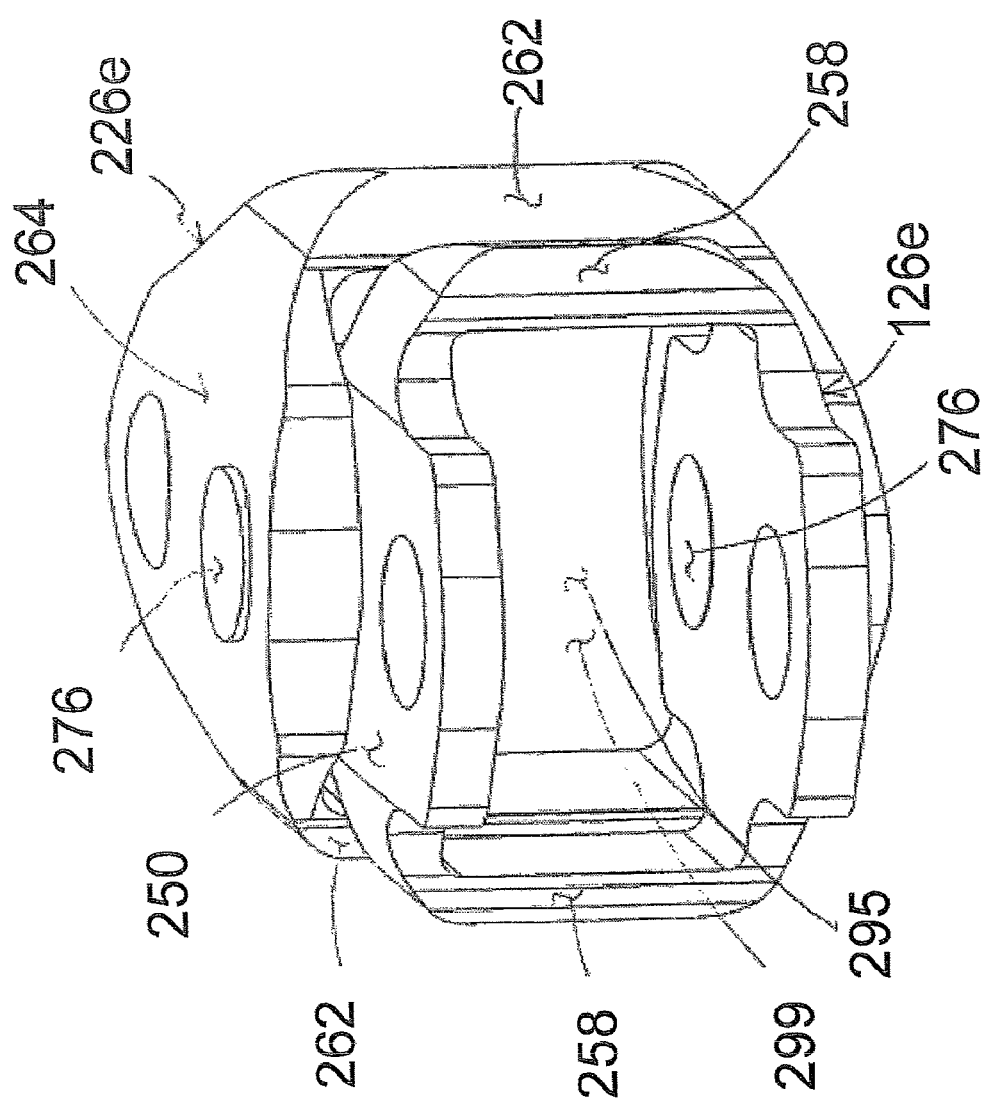

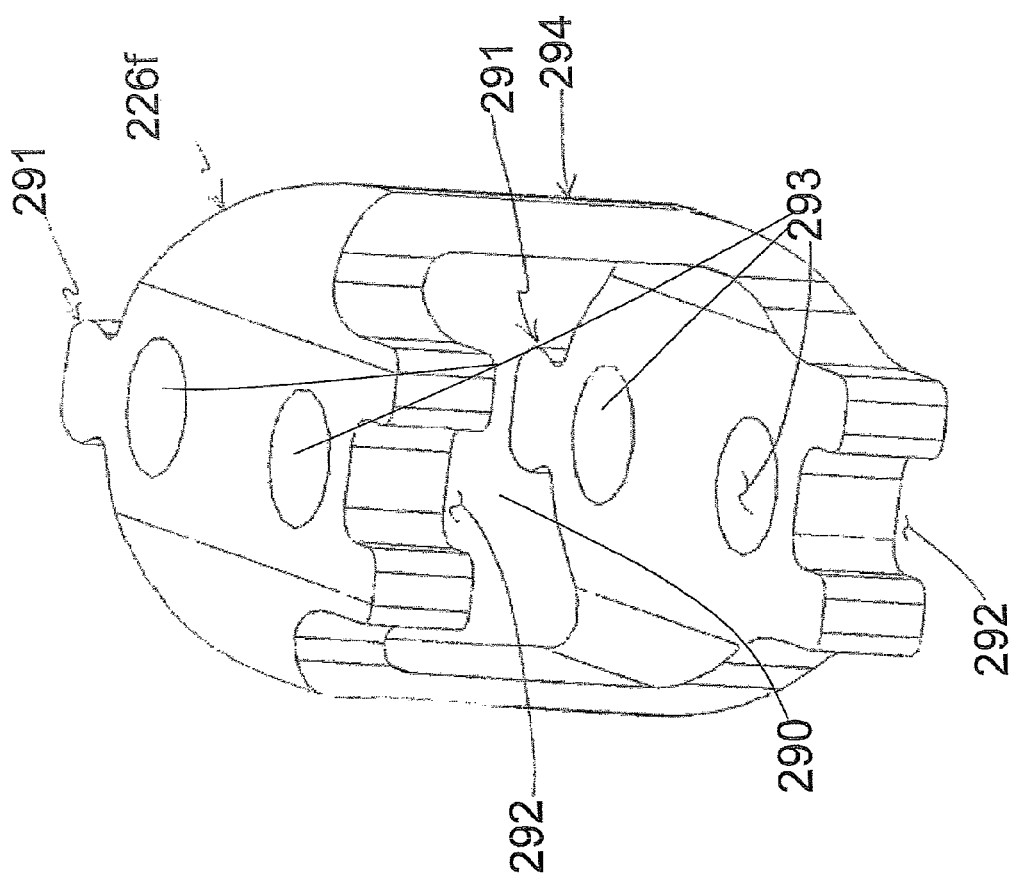

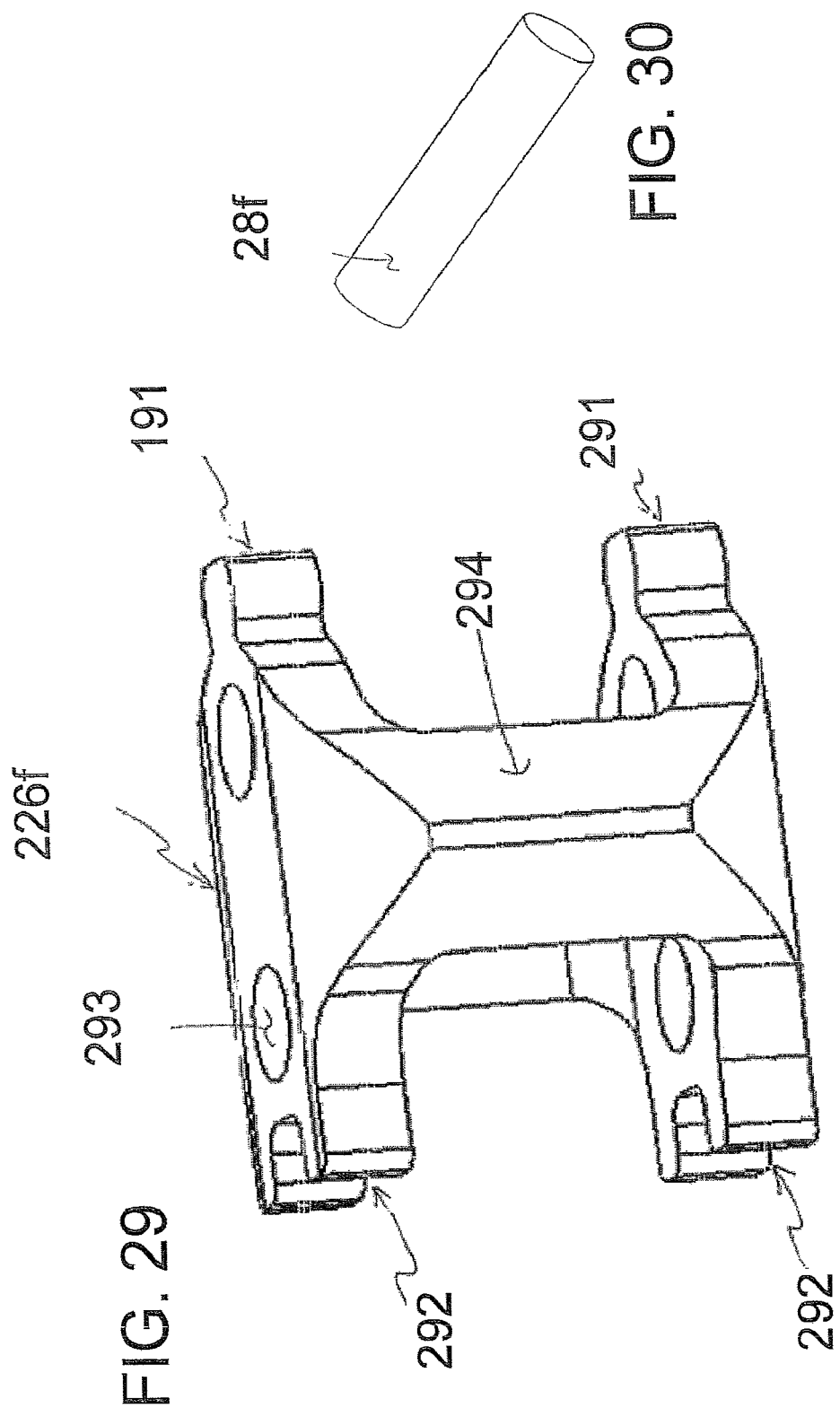

MEDICAL DEVICE WITH ARTICULATING SHAFT

RELATED APPLICATIONS

This application is a continuation in part of U.S. patent application Ser. No. 11/211,834 filed on Aug. 25, 2005 and entitled "MEDICAL DEVICE WITH ARTICULATING SHAFT," and claims priority of U.S. Provisional Patent Application Ser. No. 60/804,184 filed on Jun. 8, 2006 and entitled "METHOD OF CREATING A FLEXIBLE SHAFT," the disclosures of both applications hereby being incorporated by reference in their entirety.

BACKGROUND OF THE INVENTION

1. Field of the Invention

The invention relates generally to surgical devices and methods, and more particularly to shafts.

2. Description of Prior Art and Related Information

In various types of surgical procedures, particularly in endoscopy, a need exists for articulating, or bendable shafts. Such shafts are preferable, and often times necessary, for circumnavigating particular areas in the human body in order to reach a specific destination therein. Articulating shafts in the prior art include complex mechanisms that are expensive to manufacture and difficult to assemble. These complexities have derived, at least in part, from the need to provide tension in order to cause the shaft to bend.

Such shafts in the prior art include flexible portions which can bend in only one direction through the use of various types of tensioning mechanisms. Since the pathway to a particular desired location in a human body is often circuitous in more intricate surgical procedures, bending a shaft in only one direction can be very limiting. To overcome this deficiency, mechanisms to rotate a one-way bending shaft have been employed. Of course, having to manipulate a knob to rotate a shaft and then having to pull a tension mechanism to bend a shaft increases the complexity of a surgical procedure.

Prior art articulating shafts also include those that bend in opposite directions. Nonetheless, the bending of such shafts is accomplished by tension which means that at least two tensioning mechanisms are provided: one to cause the bend in a first direction, and the other to cause the bend in an opposite direction. Use of these types of shafts requires the technician to select the appropriate tensioning mechanism.

Articulating shafts in the prior art are also highly complex. These complexities have derived from the requirement of bending a distal portion of a shaft with a mechanism located at a proximal end of a medical device. Such complexities relate to both the manufacturing and operation of these devices. Prior art articulating shafts also lack rigidity. This is due at least in part to the fact that tensioning mechanisms in the prior art do not provide sufficient rigidity. Under standard use, prior art shafts are often unable to maintain a sufficient articulated form or shape.

No simple structure has been devised to accomplish ease of operation and flexibility with a desired rigidity.

SUMMARY OF THE INVENTION

In accordance with the present invention, structures and associated methods are disclosed which address these needs and overcome the deficiencies of the prior art.

In one aspect, a medical device comprises a bendable portion, or articulating shaft. The bendable portion is formed from a plurality of pivot members that are arranged in succession and a related plurality of pivot assemblies that pivotally connect adjacent ones of the plurality of pivot members. In one embodiment, bendable portion includes a plurality of independent pivot members and pins in an alternating configuration. In another embodiment, the bendable portion includes a plurality of overlapping members that are provided, for example, as inner links and outer links. The outer links define an aperture adapted to have the inner links substantially extended therethrough. A first slat assembly and second slat assembly extend through the bendable portion. Each of the first slat assembly and the second slat assembly is configured to push when the other of the first slat assembly and the second slat assembly pulls so as to cause the bending portion to bend.

In an embodiment involving separate pivot members, the openings collectively define an outer passageway while the pin apertures collectively define an inner passageway. The first slat assembly extends through the outer passageway alongside a first side of the pins while the second slat assembly extends through the outer passageway alongside a second side of the pins opposite the first side of the pins. The inner passageway provides a path for an actuator, a flexible tube, electrical wiring and/or light transmitting media, such as optical fibers, to extend through the bendable portion. The actuator may be formed with a variety of cross-sectional shapes, such as a rectangle, square, circle, etc.

In an embodiment involving overlapping pivot members, each of the inner links comprises a male tab and a female slot, and defines a first aperture and a second aperture, and each of the outer links comprises a male tab and a female slot. The first slat assembly extends through the first aperture of the inner links and the aperture of the outer links, and the second slat assembly extends through the second aperture of the inner links and the aperture of the outer links.

In an alternative embodiment, each of the outer links defines an aperture, and each of the inner links defines an aperture adapted to form a common channel with the aperture of each of the outer links. The inner links and outer links are connected with half pins. A gap between paired half pins defines an inner passageway. Alternatively, the inner links and outer links are connected with pins having a pin aperture, and the pin aperture defines an inner passageway.

An articulator is coupled to the first slat assembly and the second slat assembly such that operation of the articulator causes one of the first and second slat assemblies to push and the other of the first and second slat assemblies to pull simultaneously. In an embodiment, movement of the articulator in one direction causes the bendable portion to bend in an opposite direction away from the direction of movement of the articulator. Alternatively, intermediate mechanisms may be coupled to the slat assemblies and the articulator to reverse this motion such that movement of the articulator in one direction causes the bendable portion to bend toward the same direction. Each pivot member defines a vertical axis. The device may comprise means for preventing each pin from moving vertically with respect to an adjacent pivot member. Each pivot member preferably has a laterally tapered thickness.

The first slat assembly comprises at least one slat and preferably a first plurality of layered slats. The second slat assembly comprises at least one slat and preferably a second plurality of layered slats. The device further comprises a rigid shaft portion coupled proximally to the bendable portion. The bendable portion may comprise a preconfigured and permanent curve that is disposed, or bent, in a direction generally perpendicular to the range of motion of the bendable portion.

For example, the preconfigured curve may be bent upward or downward with respect to the rigid shaft portion.

In another aspect, a medical device comprises a bendable portion including a series of pivot members and pins in an alternating configuration. A first slat assembly is coupled to the bendable portion. A second slat assembly coupled to the bendable portion. The pivot members may also include inner links and outer links. The outer links define an aperture adapted to have the inner links substantially extended therethrough. Each of the first slat assembly and the second slat assembly is configured to push when the other of the first slat assembly and the second slat assembly pulls so as to cause the bendable portion to bend.

The inner links and outer links are connected with pins. Each pivot member may also comprise a male tab and a female slot, a male tab engaging a neighboring female slot of a similar link. In an alternative embodiment, each of the outer links defines an aperture, and each of the inner links defines an aperture adapted to form a common channel or passageway with the aperture of each of the outer links. The inner links and the outer links are connected with half pins or with pins having an aperture.

In a further aspect, a method is provided for articulating a shaft of a medical device. The method comprises providing pivot members each having a single opening, extending a first slat assembly through the single opening of each pivot member, extending a second slat assembly through the single opening of each pivot member, pushing one of the first and second slat assemblies while concurrently pulling the other of the first and second slat assemblies to cause the pivot members to collectively form a bend.

The method further comprises providing an alternating plurality of inner link pivot members and outer link pivot members, each pivot member having an opening to collectively form a passageway, connecting adjacent ones of the pivot members to one another with a pin, extending a first slat assembly through the passageway formed by the pivot members, extending a second slat assembly through the passageway formed by the pivot members; and pushing one of the first and second slat assemblies while concurrently pulling the other of the first and second slat assemblies to cause the pivot members to collectively form a bend.

The method further comprises engaging a female slot of an inner link pivot member with a male tab of a neighboring inner link pivot member, and engaging a female slot of an outer link pivot member with a male tab of a neighboring outer link pivot member.

The step of pushing one of the first and second slat assemblies while concurrently pulling the other of the first and second slat assemblies comprises moving an articulator. The step of moving the articulator comprises moving the articulator to a left direction to cause the pivot members to collectively form a bend in a first direction, and moving the articulator to the right direction to cause the pivot members to collectively form a bend in a second direction.

The method further comprises actuating an end operating, or tool, assembly coupled distally to the articulating shaft.

In summary, a medical device includes an articulating shaft with a pair of slat assemblies. By moving an articulator, the slat assemblies are configured to concurrently push while the other pulls in order to bend the articulating shaft. The articulating shaft includes a series of pivot members formed, for example, from alternating pins and pivot members, or from inner links and outer links. The slat assemblies extend generally parallel to each other. A method for articulating a shaft of a medical device is also provided.

The invention, now having been briefly summarized, may be better visualized by turning to the following drawings wherein like elements are referenced by like numerals.

BRIEF DESCRIPTION OF THE DRAWINGS

FIG. 5 is a perspective view of a pin;

FIG. 6 is front elevation view of a pivot member and the pin;

FIG. 7 is a perspective view an alternate pin;

FIG. 10 is a top plan view of the medical device showing the first articulating shaft in a rest state;

FIG. 11 is a top plan view of the medical device in FIG. 11 showing the articulating shaft bent;

FIG. 12 is a top plan view of an alternative embodiment where the articulating shaft bends in the same direction in which the articulator is moved;

FIG. 13 is a top plan view of a further alternative embodiment where the articulating shaft bends in the same direction in which the articulator is moved;

FIGS. 17 through 22 illustrate a further embodiment of an articulating shaft, wherein, FIG. 17 is a perspective view of an articulated assembly of inner and outer links in accordance with an embodiment of the invention;

FIG. 18 is a perspective of an alternative embodiment of the inner link;

FIG. 19 is another perspective of the inner link shown in FIG. 18;

FIG. 20 is a perspective view of a half pin used to connect an inner link with an outer link;

FIG. 21 is a close-up perspective view of an inner link connected to an outer link; and FIG. 22 is another close-up perspective view of the connected inner link and outer link shown in FIG. 21;

FIGS. 23 and 24 illustrate a modification to the embodiment of FIGS. 17 to 22, wherein, FIG. 23 is a perspective view of a pin with a pin aperture used in place of a pair of half pins; and FIG. 24 is a perspective view of an inner link and an outer link connected using the pin shown in FIG. 23;

FIGS. 25 to 34 illustrate an even further embodiment of an articulating shaft, wherein, FIG. 25 is a perspective view of an articulated assembly of inner and outer links;

FIG. 26 is a perspective view of an inner link pivot member in accordance with an embodiment of the invention;

FIG. 27 is a different view of the inner link pivot member shown in FIG. 26;

FIG. 28 is a perspective view of an outer link pivot member in accordance with an embodiment of the invention;

FIG. 29 is a different view of the outer link pivot member shown in FIG. 28;

FIG. 30 is a perspective view of a pin used to attach pivot members;

FIG. 31 is a perspective view of a portion of the shaft including connected inner and outer links in accordance with an embodiment of the invention;

FIG. 32 is a close-up perspective view of engaged inner links of a portion of the shaft;

FIG. 33 is a close-up perspective view of connected inner link and outer link of a portion of the shaft; and FIG. 34 is an illustration of constrained relative movement between the inner links and the outer links;

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The herein invention may be embodied various medical devices that include an articulating or bendable portion formed from a plurality of pivot members that are arranged in succession and a related plurality of pivot assembly that pivotally connect adjacent ones of the plurality of pivot members.

Figure 1:
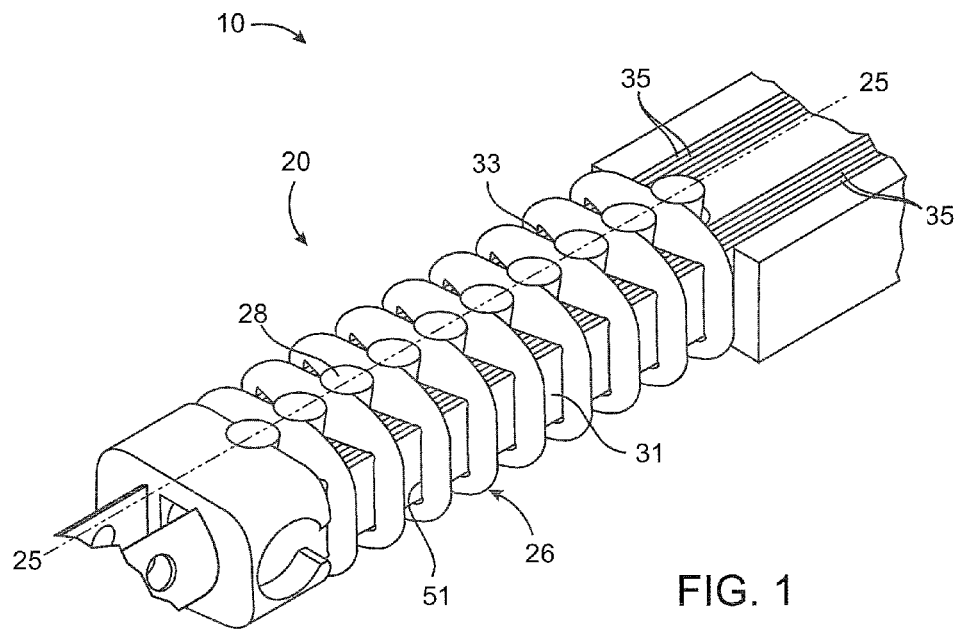
FIG. 1 is a perspective view of a first embodiment of an articulating shaft according to the invention.
Figure 2:
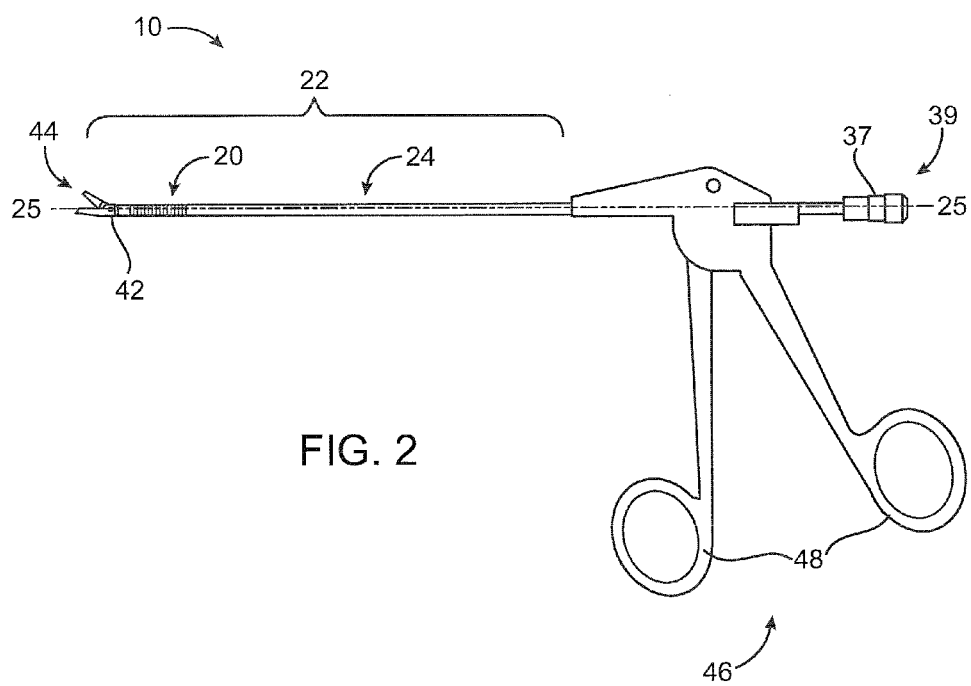
FIG. 2 is a side elevation view of a medical device according to the invention.

A first embodiment of a medical device is illustrated in FIGS. 1 and 2 and designated generally by the reference numeral 10. The medical device, or instrument, 10 is particularly configured for intricate surgical procedures where a direct, straight path to a desired destination is unavailable. In particular, endoscopic surgeries typically require circumnavigation around particular areas within the human body in order to reach a desired location for treatment.

The device 10 includes an articulating shaft, or bendable portion, 20 of particular interest to the invention. The articulating shaft 20 is formed as a distal portion of an overall shaft 22 that also includes a proximal rigid shaft portion 24. The overall shaft 22 defines a longitudinal axis 25. In the first embodiment, the articulating shaft 20 comprises a plurality of independent pivot members 26 and pins 28 disposed in an alternating configuration. Thus, each pin 28 abuts an adjacent, but separate pivot member 26 in a rotatable, or pivotable, relationship as described in further detail below.

The device 10 comprises a first slat assembly 31 and a second slat assembly 33. Each slat assembly 31, 33 comprises at least one flat, elongate slat 35 that is generally elongate, flat and thin. The slats 35 are preferably composed of a super elastic material such as Nitinol. In the embodiment, each slat assembly 31, 33 comprises a plurality of slats 35 disposed, or layered, side-by-side. Alternatively, the slat assemblies 31, 33 may include layers of other material, such as TEFLON®, disposed in between the slats 35. The slats are preferably disposed in a vertical orientation with respect to the shaft 20 so as to restrict the pivot members 26 from vertical movement. Except for the bending accomplished by the axial movement of the slat assemblies 31, 33 as described below, the slat assemblies 31, 33 also restrict individual sideways movement of any particular pivot member 26 and pin 28. In FIG. 2, the slat assemblies 31, 33 are ultimately coupled to an articulating mechanism, or articulator, 37 provided at a proximal end 39 of the device 10.

In FIG. 2, an operating mechanism 42 is coupled to the articulating shaft 20 generally at a distal end 44 of the device 10. In the illustrated embodiment shown in FIG. 2, the operating mechanism 42 is shown as forceps with a pair of jaws. It is to be expressly understood, however, that the device 10 may comprise a variety of operating mechanisms and tools at the distal end 44. As examples and not by way of limitation, the device 10 may comprise graspers, clips, suturing mechanisms, cutters, shavers, retractors, water jet cutters, RF ablation devices, imaging and/or light transmitting fibers (e.g., lasers, optical fibers, etc.) and a host of other mechanisms coupled to a distal end of the articulating shaft 20 according to the invention. Where actuation of a particular operating mechanism is necessary, the device 10 may comprise a proximal handle assembly 46 which includes a pair of handles 48, one of which is coupled to an actuator (hidden) extending through the overall shaft 22.

Figure 3:
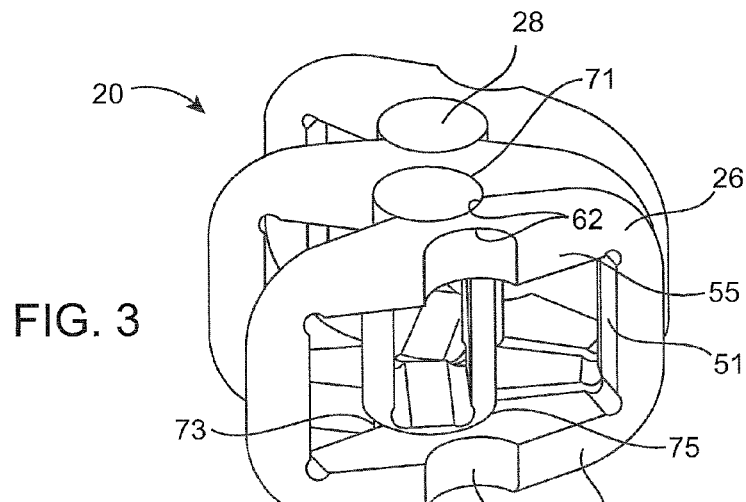
FIG. 3 is a close-up perspective view of a portion of the first embodiment of the articulating shaft.
Figure 4A:
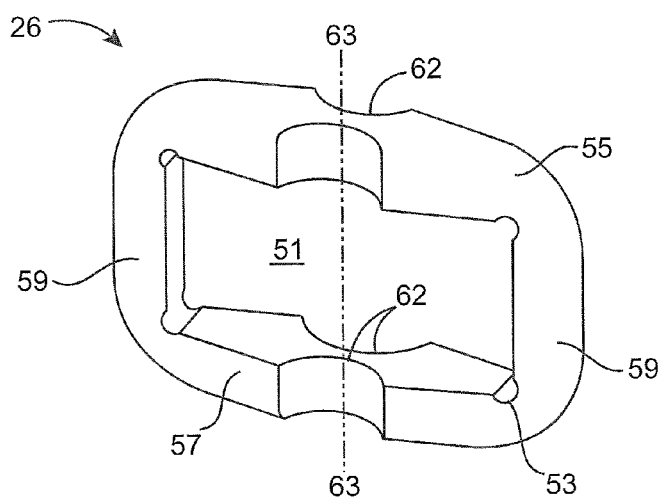
FIG. 4A is a close-up perspective view of a first pivot member of the articulating shaft.
Figure 4B:
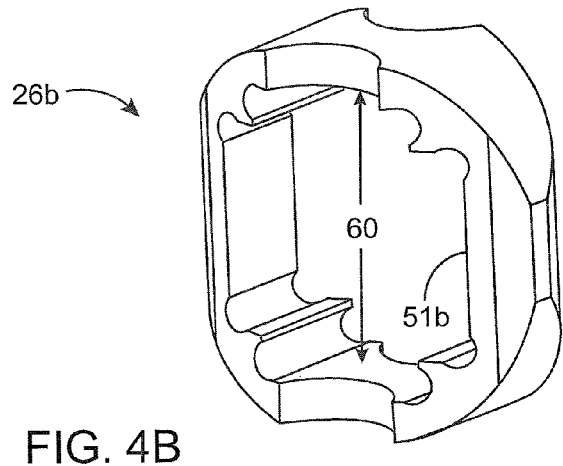
FIG. 4B is a close-up perspective view of a second pivot member of the articulating shaft.

FIG. 3 is a close-up view of a portion of the articulating shaft 20, particularly an alternating combination of pivot members 26 and pins 28 illustrated in a bent configuration. As shown in FIGS. 3 and 4A, each pivot member 26 comprises a single opening, or through hole, 51. The pivot member openings 51 may be formed in a variety of shapes and sizes. In the embodiment, the openings 51 are shaped generally rectangular. Where the openings 51 are rectangular as shown, each pivot member 26 may include rounded, or radiused, corners 53 to minimize stresses in the corners 53 and to provide sufficient clearance for slat assemblies. Each pivot member 26 includes a top portion 55 and a bottom portion 57 joined by side portions 59. The top portion 55 and bottom portion 57 have substantially similar structures. In particular, each of the top portion 55 and bottom portion 57 includes a pair of opposite curved recesses 62 for receiving pins 28, as shown in FIG. 3. The recesses 62 are smoothly curved to facilitate easy pivoting, or rotation, between each pin 28 and an adjacent pivot member 26. To better facilitate a bend in the articulating shaft, each pivot member 26 preferably has a laterally tapered thickness. In particular, the thickness of each pivot member 26 decreases from a medial portion of the pivot member 26 to the lateral, or side, portions 59. Each pivot member 26 defines a vertical axis 63 as shown in FIG. 4.

In FIG. 4A, the opening 51 of the pivot member 26 is shown as generally rectangular. As discussed further below, the articulating shaft 20 may be configured to receive slat assemblies in combination with a variety of other structures with differing sizes, such as an actuator, a tube, electrical wiring, and more. Accordingly, a further embodiment of pivot member 26b is provided and illustrated in FIG. 4B having an opening 51b with a taller central section 60 for accommodating a larger structure extending therethrough.

In FIGS. 3 and 5, the pin 28 comprises a pin aperture, or through hole, 64 that is also defined by rounded, or radiused, corners 66 to minimize stresses in the corners 66 and to provide sufficient clearance for actuators, conduits or whatever mechanism may be inserted therethrough. As described further below, the pin apertures 64 collectively define an inner passageway, or path, for receiving an actuator, a tube, electrical wiring, or light transmitting media such as optical fibers. Each pin 28 comprises a central portion 68 with an increased diameter than that of the top portion 71 and bottom portion 73 so as to form top and bottom shoulders 75. As shown in FIGS. 3 and 6, the pin shoulders 75 restrict vertical movement between the pin 28 and an adjacent pivot member 26 by abutting the inner surfaces of the top portion 55 and bottom portion 57 of the pivot member 26. Also in FIGS. 3 and 6, the mating of the pin top portion 71 and the pin bottom portion 73 with the curved recesses 62 of the pivot members 26 centers each pin 28 with respect to an adjacent pivot member 26 while enabling free pivoting therebetween. In FIGS. 1 and 6, the openings 51 of the pivot members 26 collectively form an outer passageway through which the slat assemblies 31, 33 are inserted. As shown in FIG. 6, it will be appreciated that the embodiment of the device obviates the need for multiple lumens, or bores. By forming the pivot member 26 as a generally rectangular frame with a dominant opening 51, multiple slat assemblies may extend the pivot members 26 without need for aligning any lumens.

In an alternative embodiment shown in FIG. 7, the pin 28b may simply comprise a substantially cylindrical outer surface 77 and a pin aperture 64b.

Figure 8A:
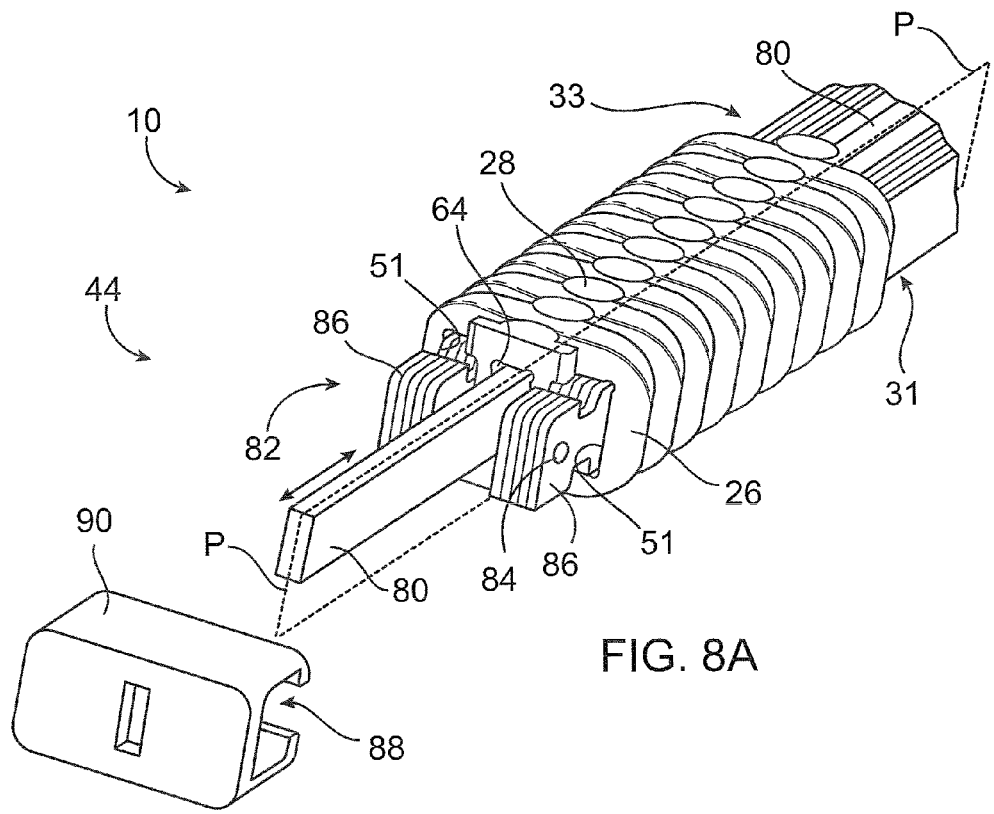
FIG. 8A is a perspective view of a medical device, illustrating the articulating shaft and a rectangular actuator.

FIG. 8A is a perspective view of a partially assembled device 10, shown with slat assemblies 31, 33 and an actuator 80 configured for reciprocating, or oscillating, movement along the axis of the shaft as indicated by the bidirectional arrows. In the illustrated embodiment, the actuator 80 has a rectangular cross-sectional profile with a height greater than its width such that, when it is in a straight configuration, the actuator 80 substantially defines a plane P. Accordingly, the actuator 80 with a rectangular profile thus has a greater elasticity, or flexibility, normal to the plane P than in the plane P. Alternatively stated, the actuator 80 can be easily bent in accordance with the range of motion of the articulating shaft, but not perpendicularly with respect to such range of motion. The actuator 80 is inserted through the pin apertures 64 so as to extend through the articulating shaft 20. The first slat assembly 31 and second slat assembly 33 are inserted through the openings 51 in the pivot members 26. The first slat assembly 31 and second slat assembly 33 extend through the articulating shaft 20 on opposite sides of the pins 28 and the centrally located actuator 80. A connecting mechanism 82 is provided at distal end of each slat assembly 31, 33. In the illustrated embodiment shown in FIG. 8A, the connecting mechanism 82 may comprise transverse slots 84 for receiving bars (not shown). The connecting mechanism 82 may also comprise particularly shaped keys 86 formed at the distal end of the slat assemblies 31, 33 and configured to fit into a slot 88 of a distal tip 90 of the articulating shaft.

Figure 8B:
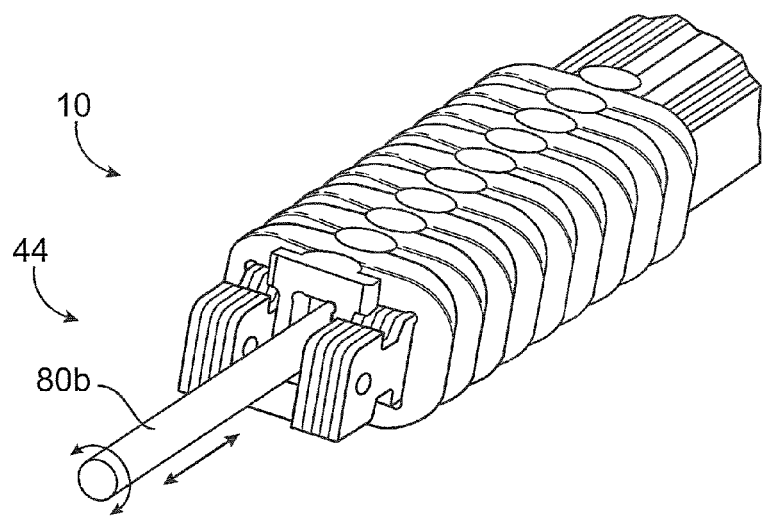
FIG. 8B is a perspective view of a further medical device with a cylindrical actuator.

In FIG. 8B, the device 10 may comprise a cylindrical actuator 80b such that, in addition to a reciprocating motion, it can be rotated to transfer a torsional force from a proximal end of the device 10 to the distal end.

Figure 8C:
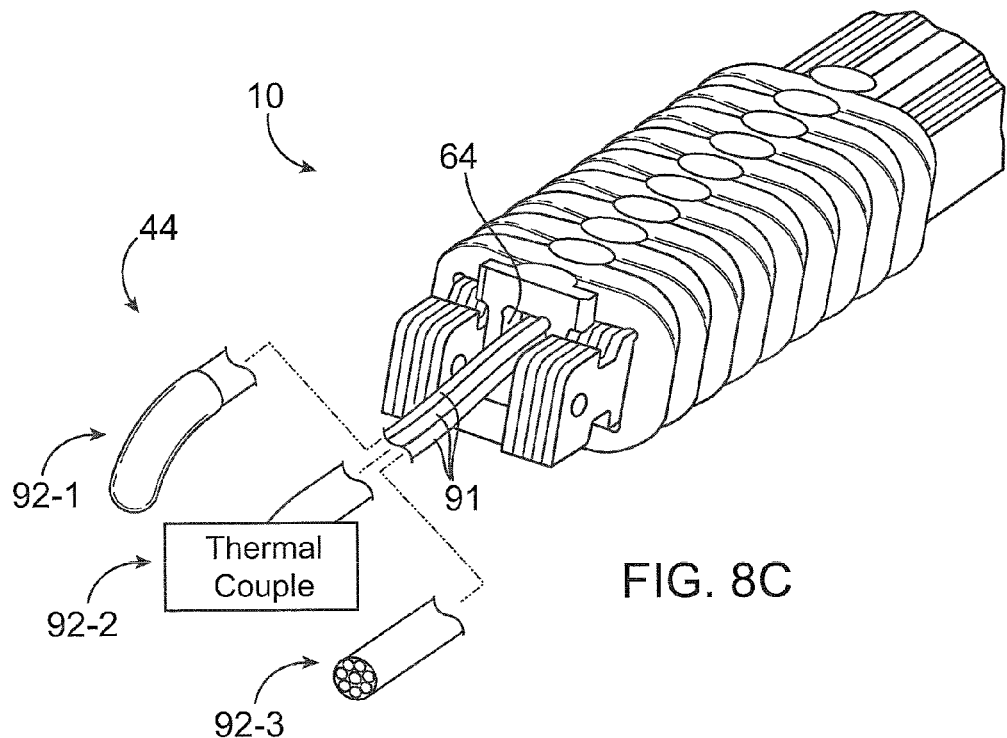
FIG. 8C is a perspective view of further embodiments having electrical wires and/or optical fibers extending through the articulating shaft and a variety of operating mechanisms.

In further embodiments illustrated in FIG. 8C, the device 10 may comprise electrical wiring or optical fibers, both designated by the numeral 91, instead of an actuator extending through the pin apertures 64. The electrical wires or optical fibers 91 may then be coupled to a variety of different operating mechanisms formed at a distal end 44 depending upon the desired application. For example, electrical wiring 91 may be coupled to an electrically activated device, such an RF ablation device 92-1 or an electrically passive device, such as a thermal couple, indicated conceptually by numeral 92-2. As a further example, optical wiring 91 may be provided and coupled to a fiber optic device 92-3, or simply terminated at the distal end 44.

Figure 9:
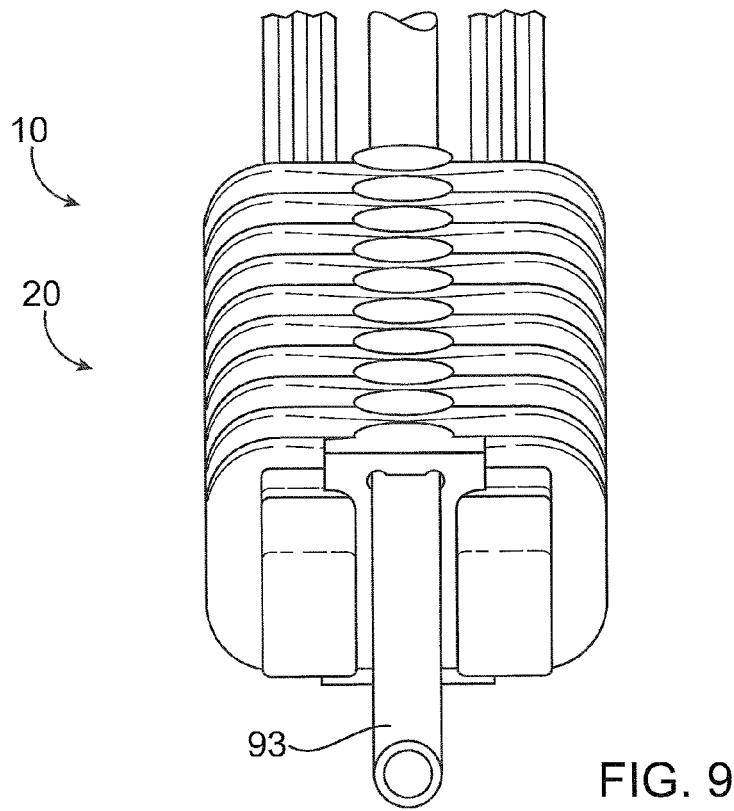
FIG. 9 is perspective view of a further medical device, illustrating the articulating shaft and a tube.

In place of an actuator, the device 10 as shown in FIG. 9 may comprise a tube, or conduit, 93 for providing a pathway or passage for fluids, needles or any other materials of interest that need to be delivered to a desired site. Thus, the articulating shaft 20 according to the invention may be incorporated into a medical device 10 in order to transport or deliver liquids, materials and/or other medical devices to areas within the human body that do not offer a direct pathway.

FIGS. 10 and 11 are top operative views of the first embodiment of the device 10. In FIG. 10, the device 10 is shown in a rest, or default, state wherein the articulating shaft 20 and articulator 37 are both straight and, thus, aligned substantially along the axis 25 defined by the rigid proximal shaft portion 24. The articulator 37, and thus the articulating shaft 20, is preferably biased to this straight position, although the device 10 may be formed such that the articulator 37 and articulating shaft 20 are biased to a non-straight, off-axis position.

In FIG. 11, the bending, or articulating, of the articulating shaft 20 is illustrated. In particular, the articulator 37 may be bent in a first direction indicated by arrow 94a, thereby causing the articulating shaft 20 to also bend in an opposite direction 94b. When a user moves the articulator 37 in the first direction 94a, the first slat assembly 31 is pulled, or tensioned, while the second slat assembly 33 is concurrently pushed, or compressed. Unlike certain articulating shafts in the prior art which operate solely by tension, the device 10 according to the invention operates by employing both push and pull forces simultaneously. It will also be appreciated that the dual opposing forces are caused by a single movement of the articulator 37.

In a similar manner, the articulator 37 may be bent in a second direction as shown by phantom lines and indicated by arrow 96a, thereby causing the articulating shaft 20 to also bend in an opposite direction 96b as a result of the first slat assembly 31 being pushed while the second slat assembly 33 is concurrently pulled.

An appreciable advantage of the device 10 is that the articulator 37 is intentionally located for convenient operation by a user. Though it is to be expressly understood that there a variety of ways to move the articulator 37, one appreciable advantage of the device 10 is that the articulator 37 can be moved by the thumb of the same hand holding the handle assembly. Thus, in the embodiment, the articulator 37 is disposed adjacent to and above the handles 48 as shown in FIG. 2. By positioning the articulator 37 in this highly desirable location, it will be appreciated that, where an actuator is employed, the user may both articulate the shaft 20 and actuate the device 10, all with one hand. Though the user may choose to use the other hand to move the articulator 37, it is not required. Instead, the user can simply leave his or her thumb on the articulator 37 at all times to move the articulating shaft 20 to the right or left as desired.

In embodiments disclosed herein, it will be appreciated that the dual slat assemblies 31, 33 provide sufficient rigidity to the articulating shaft 20. In particular, the dual slat assemblies 31, 33 rigidly maintain the articulating shaft 20 in its straight or bent form without deflection. Though each slat assembly 31, 33 may comprise a single slat, the rigidity of the articulating shaft 20 is enhanced by each slat assembly 31, 33 comprising a plurality of layered slats. Furthermore, by orienting the slats in the vertical direction, the slat assemblies 31, 33 not only rigidly hold the shape of a bent articulating shaft 20, but also prevent any vertical deflection of the articulating shaft 20.

In this embodiment, the articulating shaft 20 is configured to bend in a direction opposite to the manipulated direction of articulator 37. For example, from the vantage point of the user (i.e., looking at the device 10 from the rear), when the articulator 37 is bent to the right, indicated by arrow 94a in FIG. 11, the articulating shaft 20 bends to the left as indicated by arrow 94b in FIG. 11. The device 10 may be configured to reverse the bending motion shown in FIG. 11, such that the articulating shaft 20 bends in the same direction as the articulator 37. Thus, different mechanisms may be employed to reverse the directions of the pushing and pulling forces caused by movement of the articulator 37. In FIG. 12, for example, a set of gears 97 may be provided at the proximal end of the slat assemblies 31, 33 and coupled to the articulator 37. A variety of intermediate links and coupling mechanisms may be employed to couple the slat assemblies 31, 33 to the gears 97. In the embodiment shown in FIG. 12, moving the articulator 37 in a first direction 94a now causes the articulating shaft 20 in bend in the same direction 94b. In particular, moving the articulator to the right 94a will push the first slat assembly 31 and simultaneously pull the second slat assembly 33. Accordingly, moving the articulator 37 in the second direction 96a will cause the articulating shaft 20 to also bend in a similar direction 96b. It should also be appreciated that the articulating shaft 20 may be configured to bend to a greater or lesser degree. In the illustrated embodiment in FIG. 12, the articulating shaft 20 is illustrated with a bend greater than 90° from the axis 25 such that the distal end 44 of the device 10 is now pointing in a proximal direction toward the proximal end 39 of the device 10.

In a further alternative embodiment shown in FIG. 13, this "same-side" bending may also be accomplished without gears by crisscrossing the slat assemblies 31, 33. Moving the articulator 37 in a first direction 94a pushes the first slat assembly 31 and pulls the second slat assembly 33 such that the articulating shaft 20 also bends in a similar direction 94b as the articulator 37. Accordingly, moving the articulator in the second direction 96a will cause the articulating shaft 20 to also bend in a similar direction 96b. To enable the slat assemblies 31, 33 to criss-cross, the slat assemblies 31, 33 may be disposed on different planes, for example, or provided with slots to enable one assembly to intersect the other. It will be appreciated that a variety of mechanism may be used to accomplish the crisscrossing between the slat assemblies 31, 33.

Figure 14:
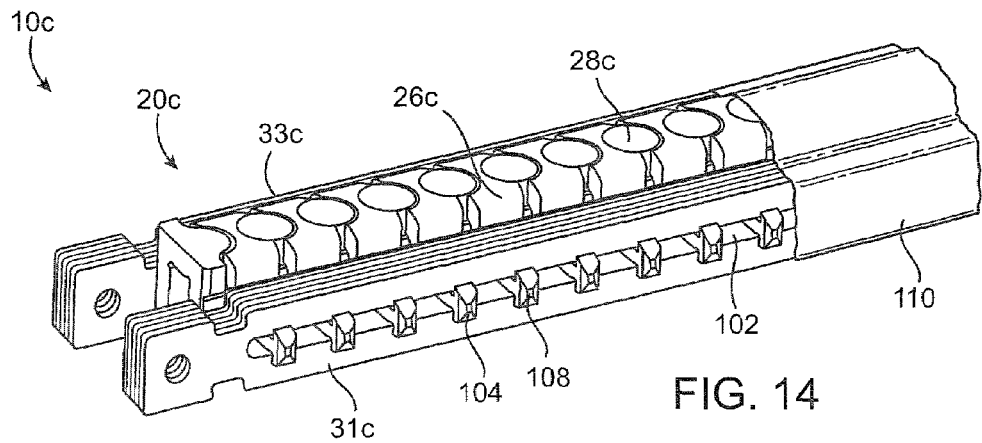
FIG. 14 is a perspective view of an alternate embodiment of an articulating shaft.
Figure 15:
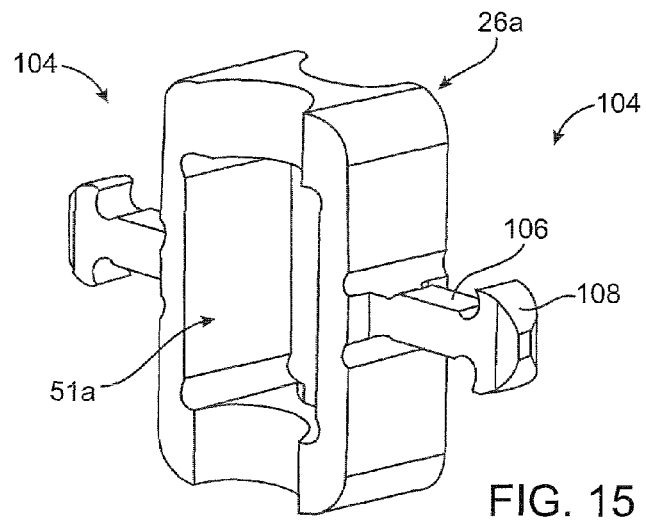
FIG. 15 is a perspective view of an alternate pivot member of the articulating shaft in FIG. 14.

FIG. 14 is a perspective view of an alternative embodiment of a device 10c including an alternative articulating shaft 20c where elements of similar structure are designated by the same reference numerals followed by the lower case "c". In FIG. 14, the device 10c includes a first slat assembly 31c and a second slat assembly 33c, each having an elongate slot 102. The shaft 20c includes a series of alternating pivot members 26c and pins 28c. In FIG. 15, each pivot member 26c includes an opening 51c, and a pair of oppositely extending arms 104. Each arm 104 includes a neck 106 and a lateral tab 108. When assembled, the arms 104 of the pivot members 26c extend laterally through the elongate slots 102 of the slat assemblies 31c, 33c as shown in FIG. 14. The lateral tabs 108 secure the pivot members 26c to the slat assemblies 31c, 33c. The device 10c may also include a sheath 110, shown partially here, over the articulating shaft 20c. It is to be understood that the sheath 110 may be provided in all of the previously disclosed embodiments.

Figure 16:
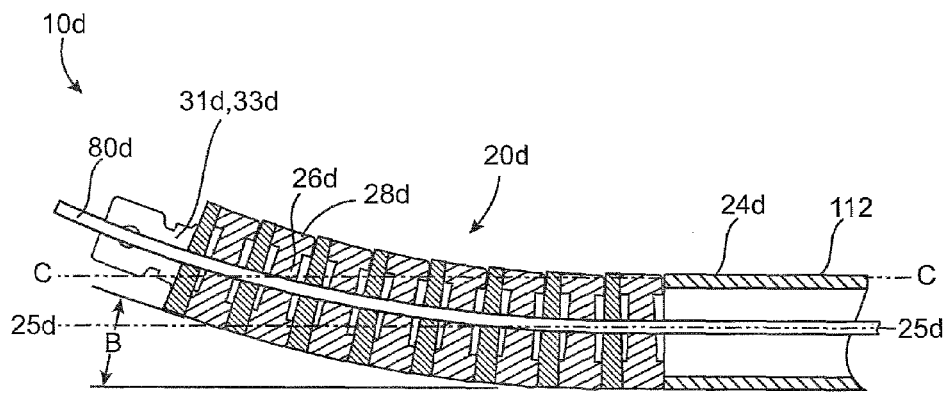
FIG. 16 is a side elevation view of a further alternate embodiment of an articulating shaft.

FIG. 16 is a side elevation view of a further alternative embodiment of a device 10d having a permanent, preconfigured curve. In this embodiment, elements of similar structure are designated by the same reference numerals followed by the lower case "d". In the illustrated embodiment, the articulating shaft 20d is permanently curved to an angle B in a direction that is generally perpendicular to the two-way bending (i.e., range of motion) of the articulating shaft 20d. Alternatively stated, the articulating shaft 20d is preferably configured to bend to the right and left directions, which directions collectively define the range of motion of the articulating shaft 20d. The articulating shaft 20d thus comprises a permanent, preconfigured curve that is perpendicular to this range of motion. The articulating shaft 20d includes pivot members 26d and pins 28d substantially similar in structure to the first embodiment described above in connection with FIGS. 1-11 except that the pivot members 26d and pins 28d may have tapered top portions to better facilitate the permanent upward curve. Here, the permanent curve is in an upward direction while the articulating shaft 20d is bendable to the right and left directions. Accordingly, the slat assemblies 31d, 33d comprise slats formed with permanent curves that conform to the permanent curve of the articulating shaft 20d. The device 10d also includes an actuator 80d that is bent in conformity with the permanent curve of the shaft 20b. It is to be expressly understood that the articulating shaft 20d may be formed with a permanent curve in any direction off the axis 25d of the rigid proximal shaft portion 24d. Accordingly, where a permanent downward curve is formed in the articulating shaft, the pivot members 26d and 28d may be formed with tapered lower portions.

Alternatively described, the device 10d in FIG. 16 includes a rigid shaft portion 24d with a top surface 112 that defines a plane C. The articulating shaft 20d includes a permanent curve that is bent in a direction away from the plane C. Here, the permanent curve of the articulating shaft 20d is shown as being perpendicular to the plane C, namely, upward.

In each of the foregoing embodiments, the articulating shaft is formed from independent pivot members and a plurality of pins disposed in an alternating configuration. But, in accordance with further embodiments of the invention, the articulating shaft may be formed from interconnected pivot members or links. The following description of several such embodiments generally uses like figures for like elements.

FIGS. 17 through 22 illustrate an embodiment where an articulating shaft 20e is formed from a succession of interconnected pivot members comprised of inner links 126e and outer links 226e. Here, the inner and outer links 126e, 226e are connected to one another by half pins 28e. As explained more fully below, one or more working channels are formed along the length of this articulating shaft 20e to allow items, such as articulating slats, actuators, torque mechanisms, etc., to pass there along, as described earlier.

FIG. 18 is a perspective view of one inner link 126e. As shown, the inner link 126e comprises two plates 250 with two pin holes 257, and two side walls 258. The two plates 250 and two side walls 258 form an aperture or through space 259.

Figure 19:
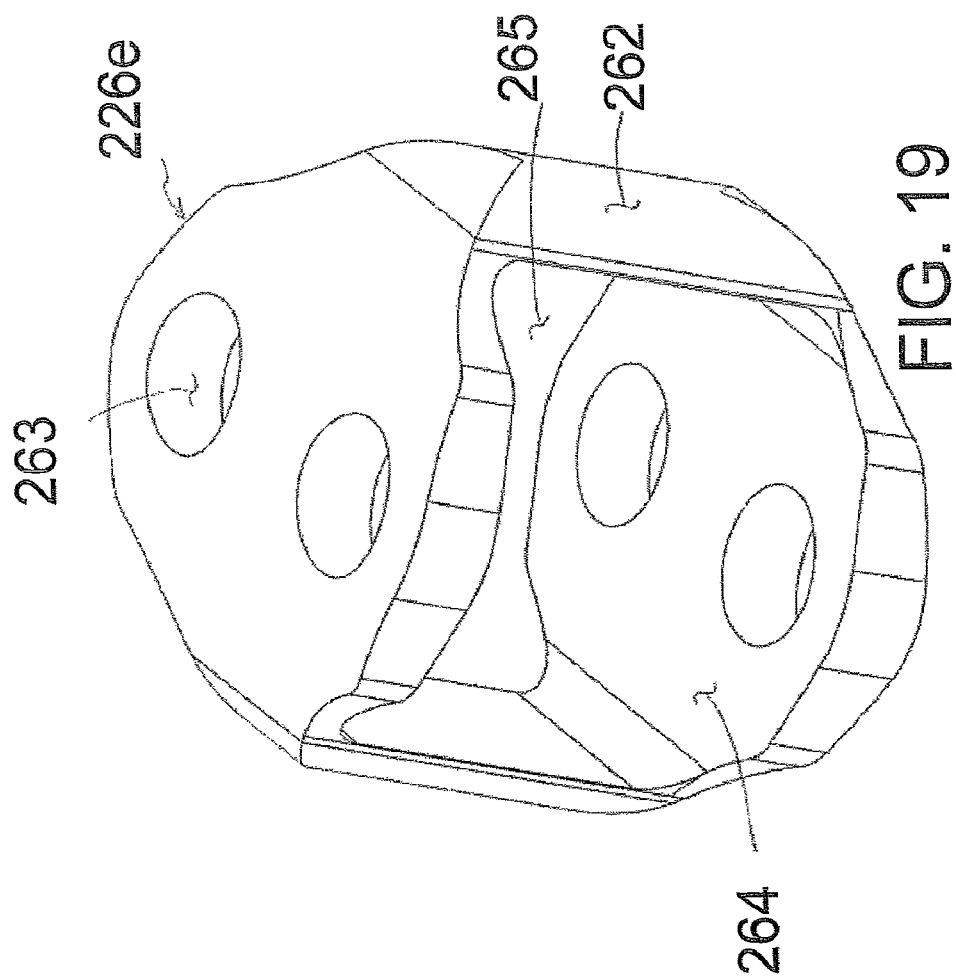

FIG. 19 is a perspective view of one outer line 226e. As shown, the outer link 26h also has two plates 264 with two pin holes 263, and two side walls 262. The two plates 264 and the two side walls 262 also form an aperture or through space 265.

Figure 20:
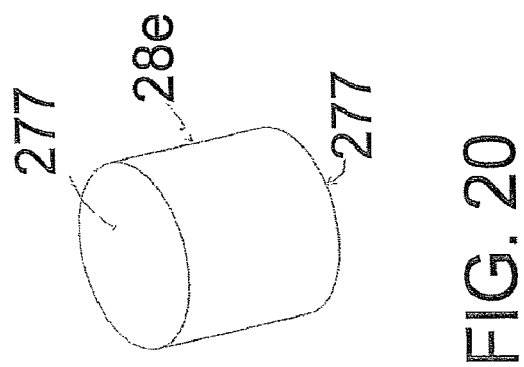

A half pin 28e, as shown in FIG. 20, is roughly a cylindrical solid and is used to connect the outer link 226e with the inner link 126e. Many variations of the half pin 28e may be recognizable to those skilled in the art. For example, the ends 277 do not need to be parallel and/or flat. A variation of the half pin 28e includes having a shoulder on one or both ends that can be larger or smaller than the pin diameter. This can aid in fixation and/or manufacturing.

As shown FIG. 21, an inner link 126e is attached to an outer link 226e with two half pins 28e. After the inner link 126e is slid inside the outer link 226e, the half pins 28e are slid into the aligned outer link pin hole 263 and the corresponding inner link pin hole 257. The half pins can be held in place with a variety of methods such as press fitting, gluing using adhesive, laser welding, etc. The half pin 28e is free to rotate relative to at least one of the holes such that the inner link 126e can rotate relative to the outer link 226e.

FIG. 22 is another view of the same assembly shown in FIG. 21. In this view, it is apparent how the two sets of side walls (258 and 262) and two sets of plates (250 and 264) combine to create a long working channel 299, which can be utilized in a variety of ways as described earlier. Another channel 295 is formed between gaps of paired half pins 28e, which as shown is a part of the working channel 299, and may be considered an "inner" passageway.

Figure 24:
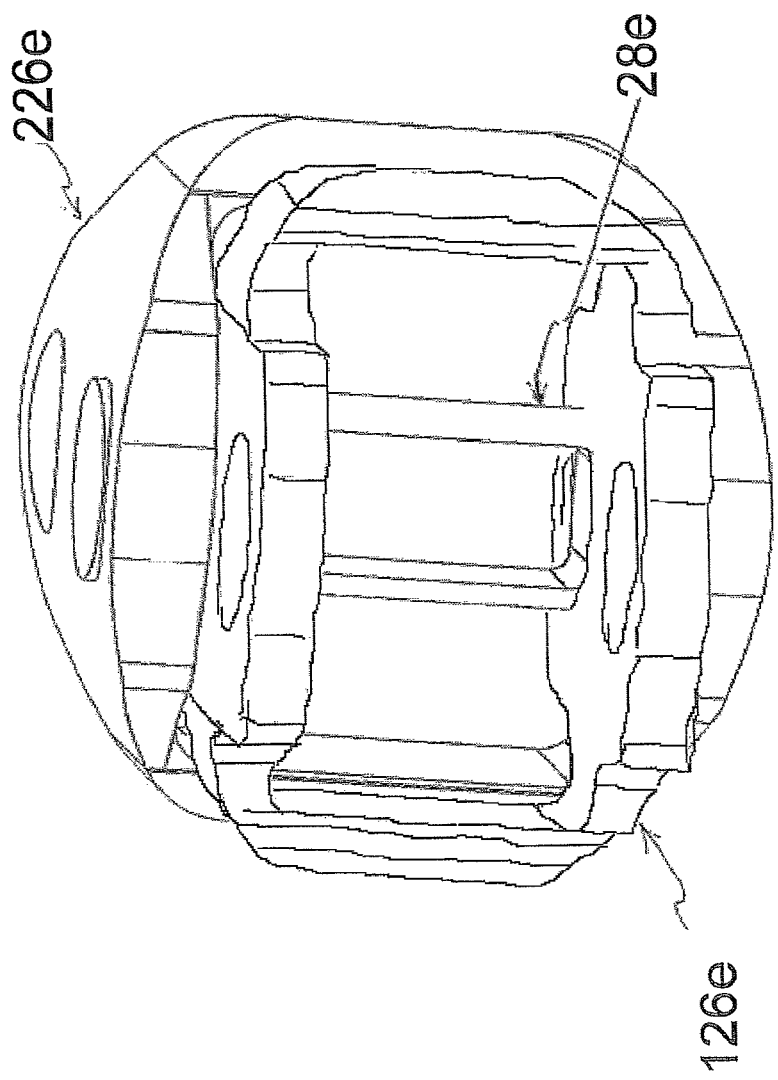
Figure 23:
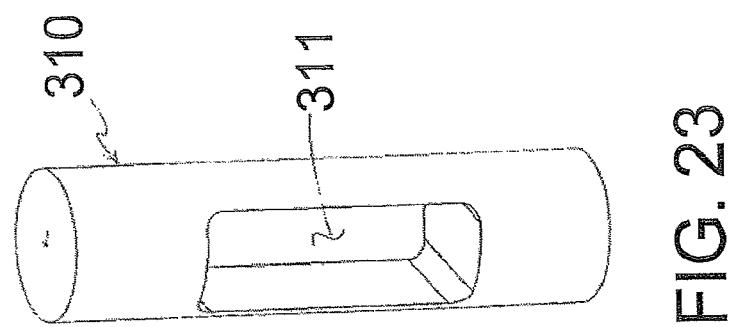
Figure 33:
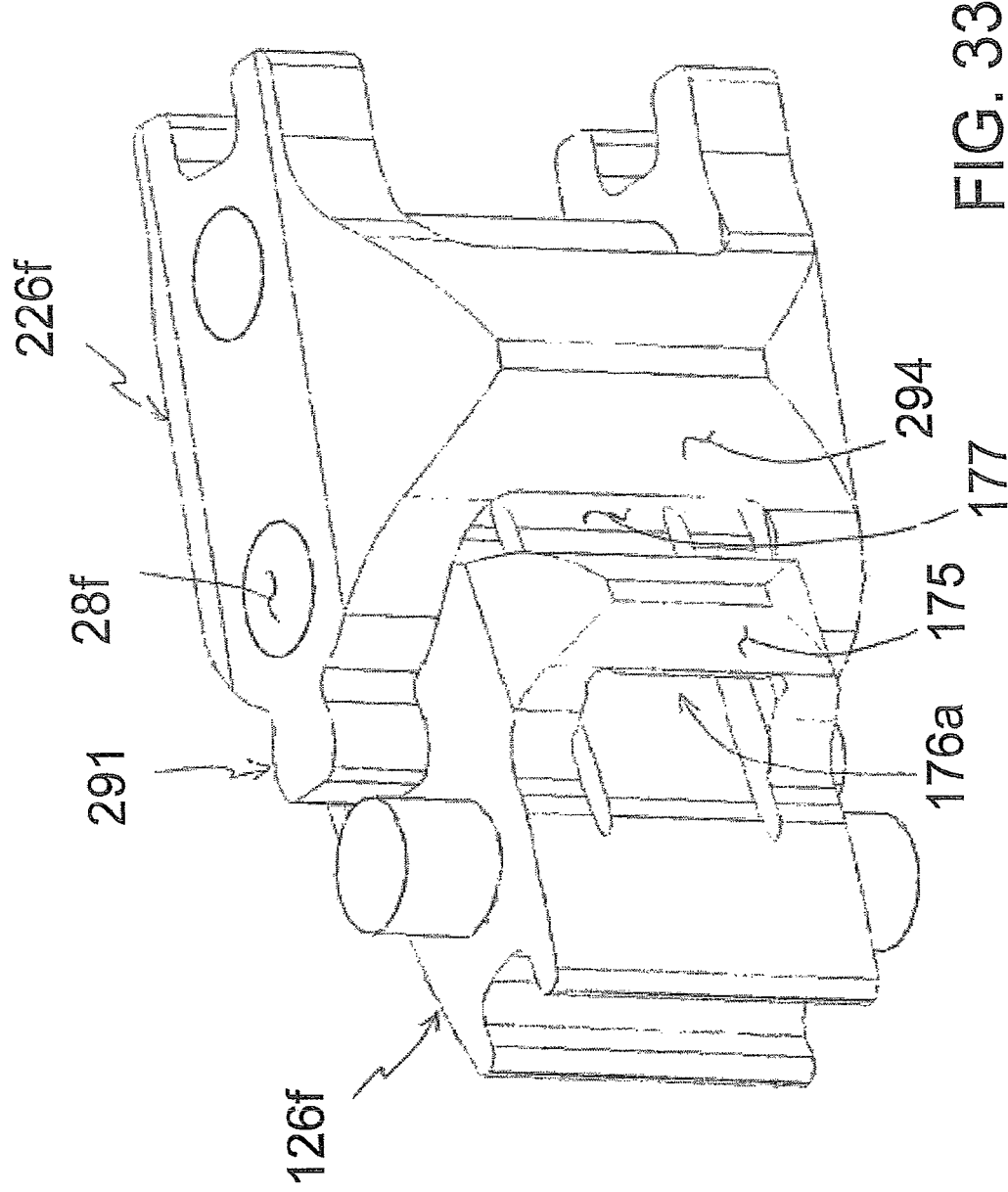

FIGS. 23 and 24 show a further embodiment relative to that of FIGS. 17 to 22. Here, in place of the half pin 28e, a slotted pin 28e' is used which, as shown in FIG. 33, is longer and contains a pin slot or aperture 311. In the assembly, this pin goes through two sets of pin holes 257 and 263 of the links such that it bridges the gap between the two sets of plates 250 and 264. The pin can be attached to none, one or both sides but must not be connected to both plates on one side (e.g. 250 and 264 on FIG. 22) because that would restrict relative rotational movement of the outer link 226e to the inner link 126e is restricted. The pin slot or aperture 311 acts as a continuation of, and helps define or maintain the links' working channels 299 and 295 (see FIG. 22).

An assembly with this pin 28e' is shown in FIG. 24. The assembly is similar to that of FIG. 22 except the two half pins 28e are replaced by one slotted pin 28e'. The pin slot or aperture 311 now defines the inner passageway in place of the gap between two half pins.

FIGS. 25 through 34 illustrate another embodiment where an articulating shaft 20f is also formed from a succession of interconnected pivot members comprised of inner links 126f and outer links 226f.

Figure 25:
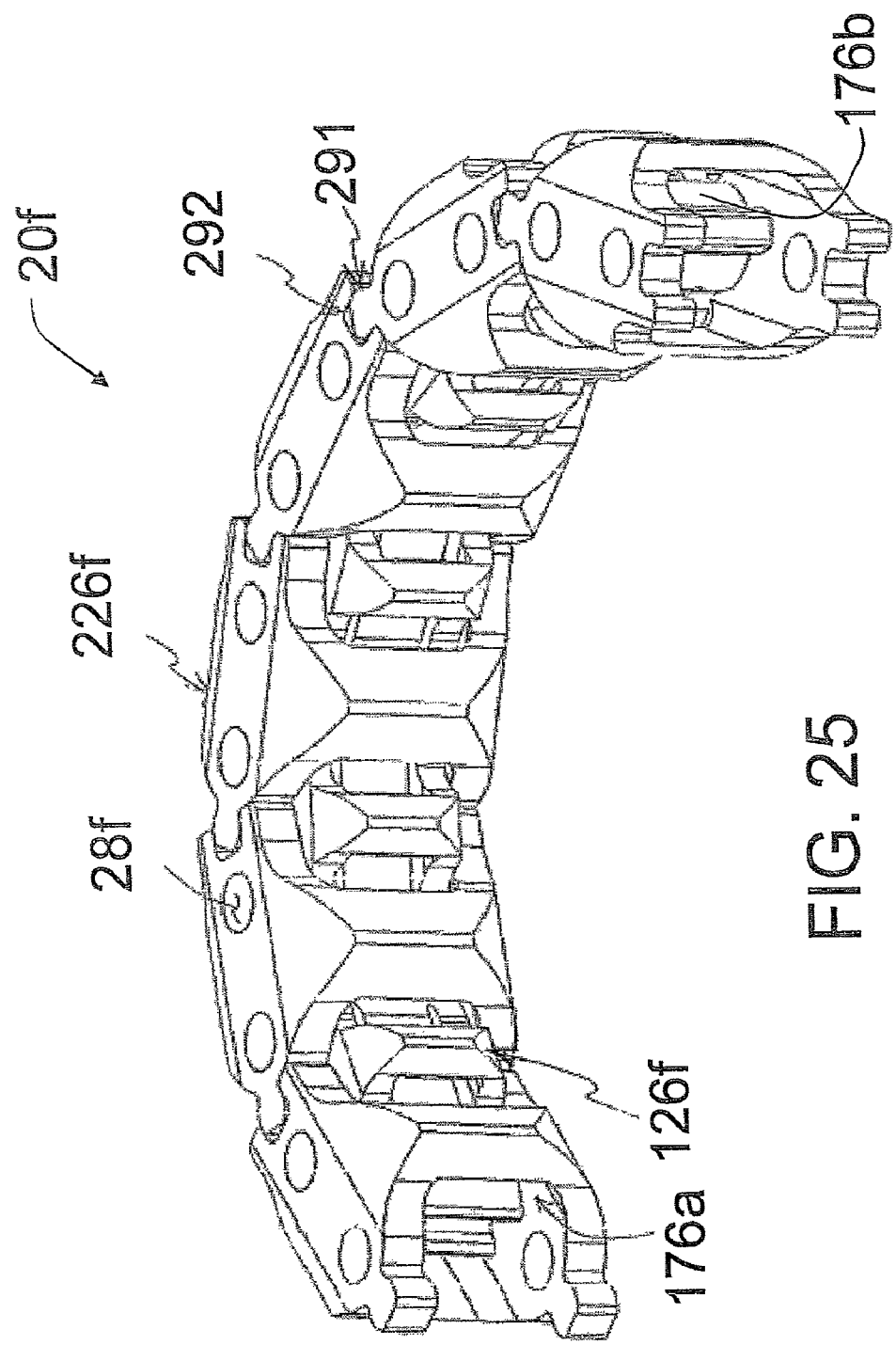

However, as shown in FIG. 25, the inner and outer links 126f, 226f of the articulating shaft 20f are connected links of opposite type by full-height pins 28f. Moreover, as more fully described below, the inner links 126f and outer links 226f are connected to adjacent links of similar type by male locking tabs and female locking slots. Two slat holes 176a and 176b extend along the length of the assembly.

Figure 26:
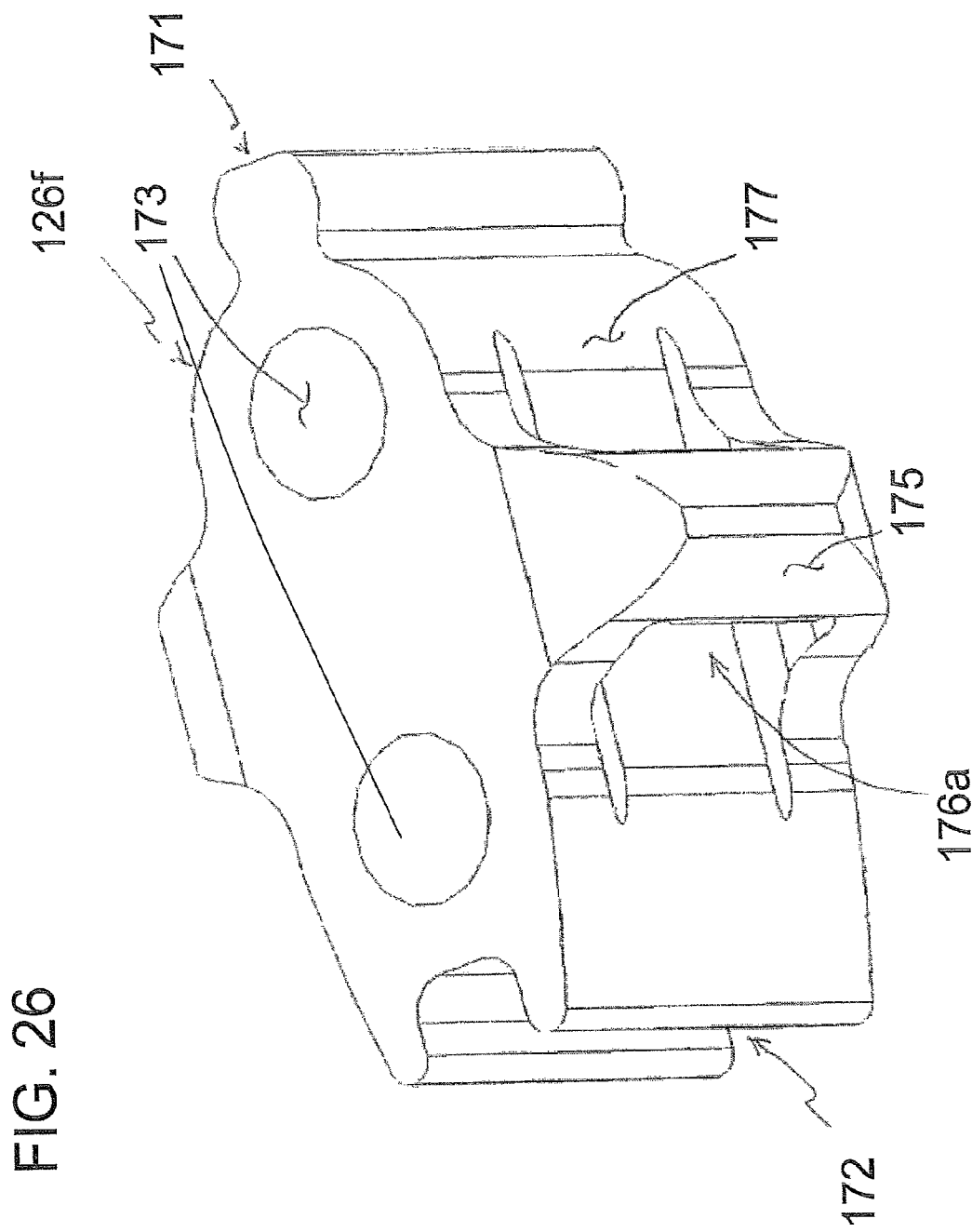
Figure 27:
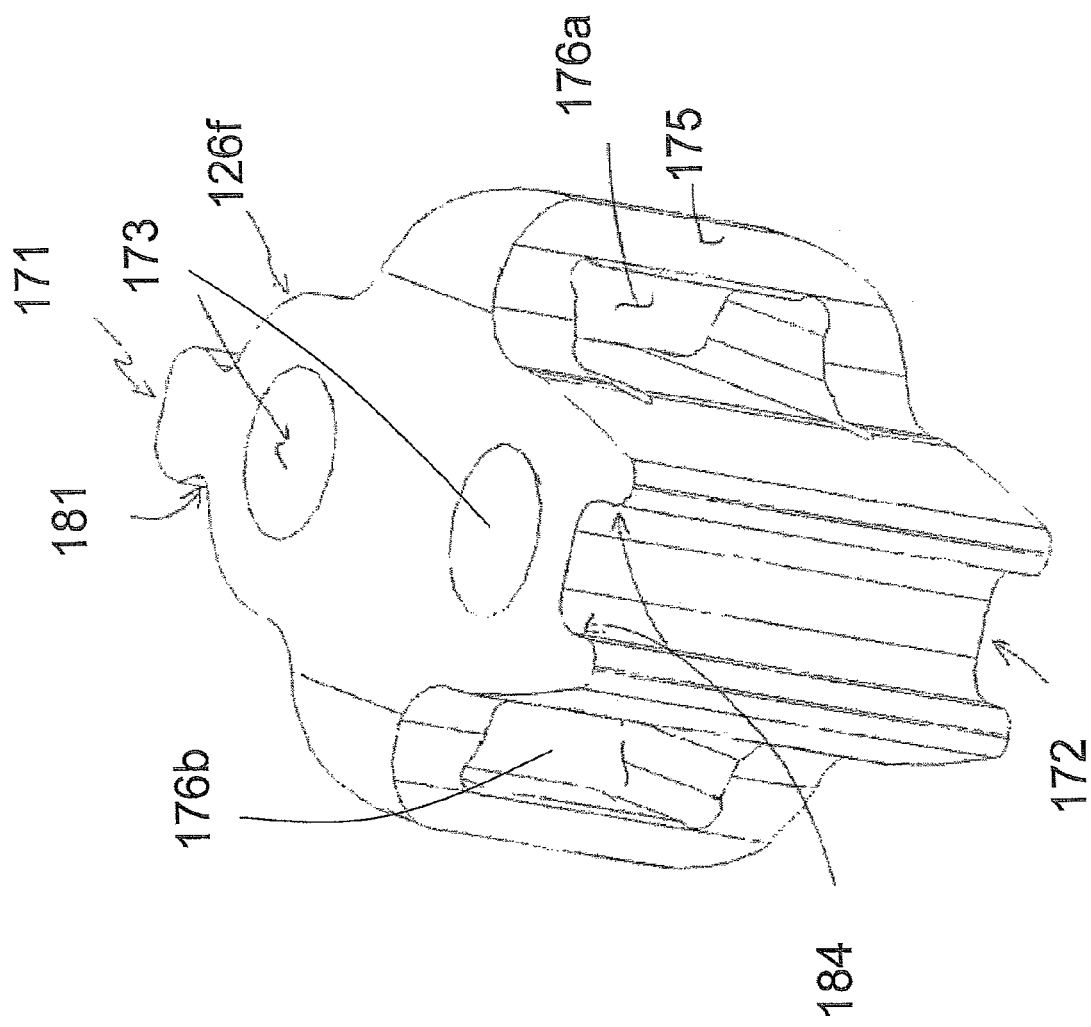

FIGS. 26 and 27 are perspective views of one inner link 126f. As shown, an inner link 126f comprises a male locking tab 171 and a female locking slot 172. The female locking slot 172 may be formed, for example, with two extrusions 184.

The inner link 126f has two pin holes 173 and 174 extending therethrough. A side wall 175 and an outer surface 177 of the main body of the inner link 126f define a first aperture 176a, which is adapted to have a first slat extended therethrough. A second aperture is also defined, as a second slat hole 176b, on the other side of the inner link 126f. FIG. 27 provides a perspective view of the inner link 126f from the direction of the female locking slot 172.

FIGS. 28 and 29 are different perspective views of one outer link 226f. The outer link 226f also has male locking tabs 291 and female locking slots 292, and four pin holes 293. The side walls 294 connect the top and bottom portions of the outer link 226f, and will act as a constraint for the slats once assembled. The side walls 294 and the top and bottom portions of the outer link 226f form an aperture 290. The aperture 290 is sufficiently large for the inner link 126f to slide in.

FIG. 30 shows the pin 28f used to connect the links during assembly. The pin 28f does not need to have an aperture.

Figure 31:
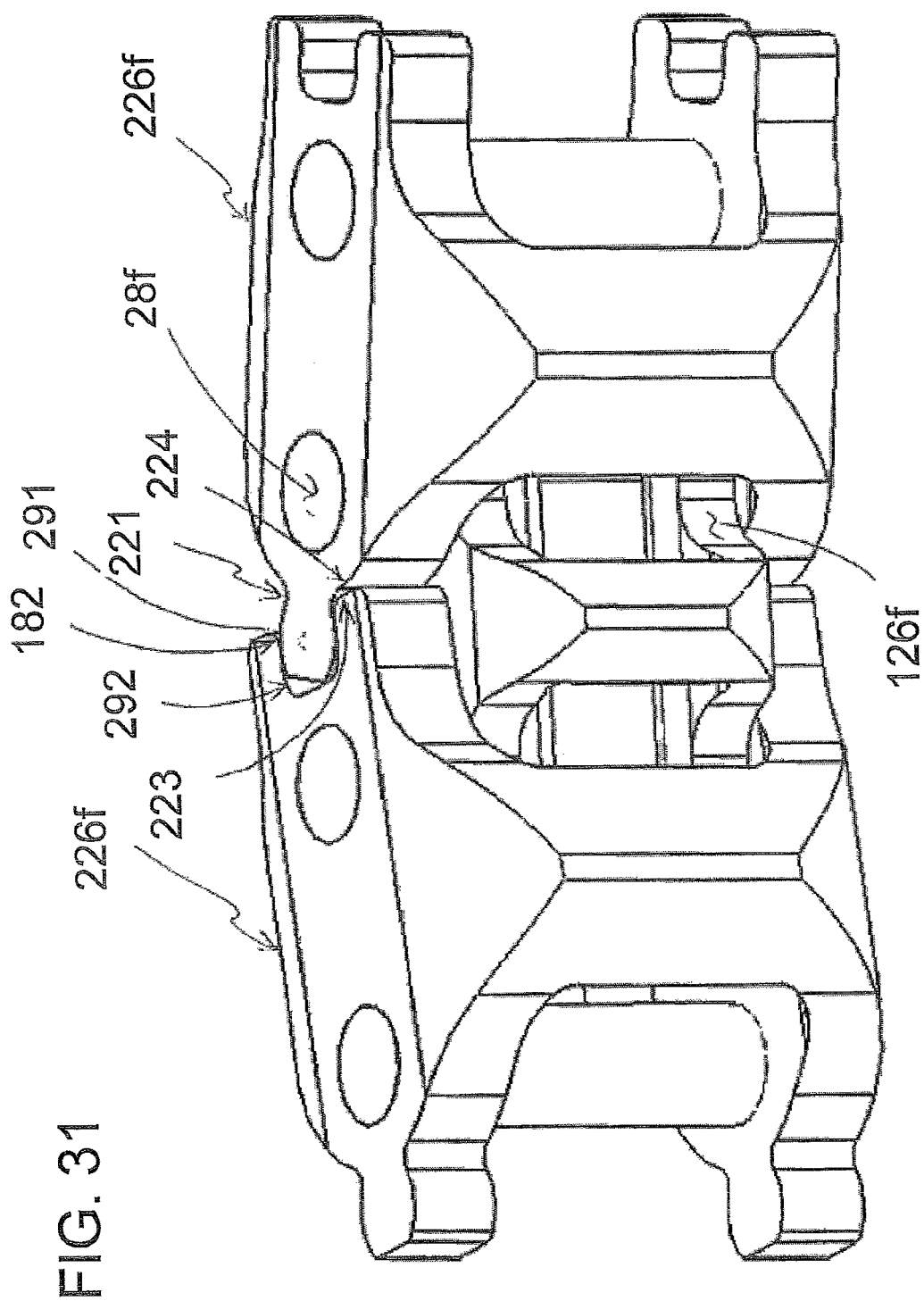
Figure 32:
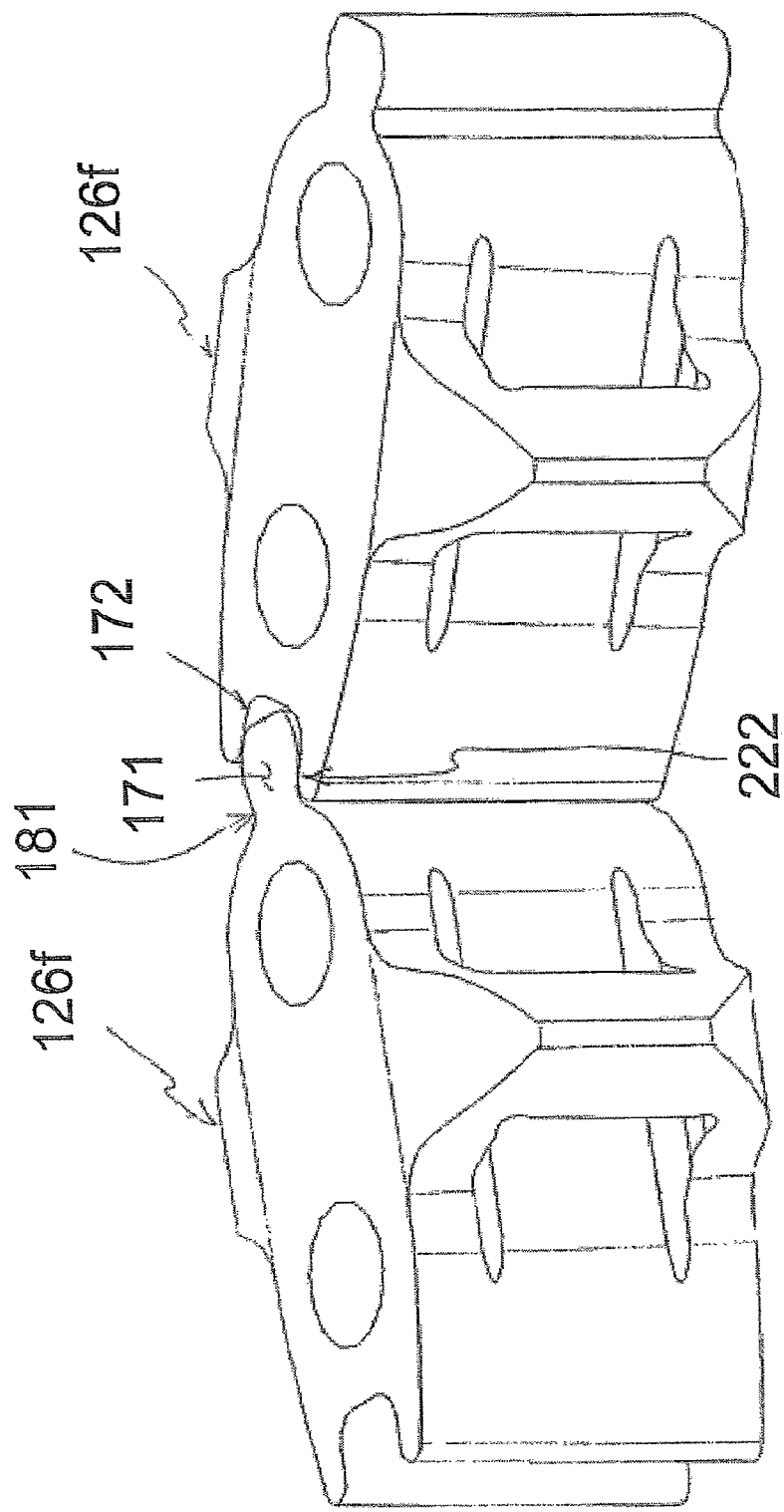

FIG. 31 is a partial assembly of two outer links 226f connected to an inner link 126f. The male locking tab 291 of one outer link 226f is placed in the female locking slot 292 of another, neighboring outer link 226f. The same tab lock assembly pertains to the Inner links 126f, where the male tab 171 one inner link 126f is placed in the female slot 172 of an adjacent inner link 126f as shown in FIG. 32.

It is recognizable to those skilled in the art that for both the outer links and the inner links, there are many variations in the male/female design combinations that may be implemented.

A series of inner links are placed within a series of outer links through the outer link aperture 290, and neighboring links (inner to outer) are pivotally connected with pins 28f. The design of the male tabs (171 and 291) and the female slots (172 and 292) allows for some relative movements between the outer link and the inner link.

The tabs also define the angular correlation between two adjacent, similar links while they are both connected to one dissimilar common link. The tab neck design (181 and 221) may also be used restrict the relative motions of two similar links to a maximum degree of rotation if desired, by creating a material interference after a certain amount of rotation.

One way of restricting the relative motions is to vary, as suggested by FIG. 31, the shape and/or the length and width of the male locking tab neck (181 and 221) relative to the female locking slot opening (182 and 222). Another way to restrict movement is to have the two mating pieces interfere with each other in a bumper-type design, shown in FIG. 31 as the female bumper 223 and the male bumper 224. As the links rotate relative to each other, the male bumper 224 and the female bumper 223 will hit each other and restrict further rotation. Each of these methods can be performed on the inner and/or outer links.

FIG. 33 is a more detailed illustration of an outer link 226f and an inner link 126f, held by a pin 28f. Though the inner and outer links can be oriented in different ways, it is preferable for the male/female direction of the two links to be oriented in opposite directions as shown. This makes for a more consistent curve when articulated. The slat hole 176a is now extended with the passage created by outer link side wall 294 and the inner link outer surface 177.

Figure 34:
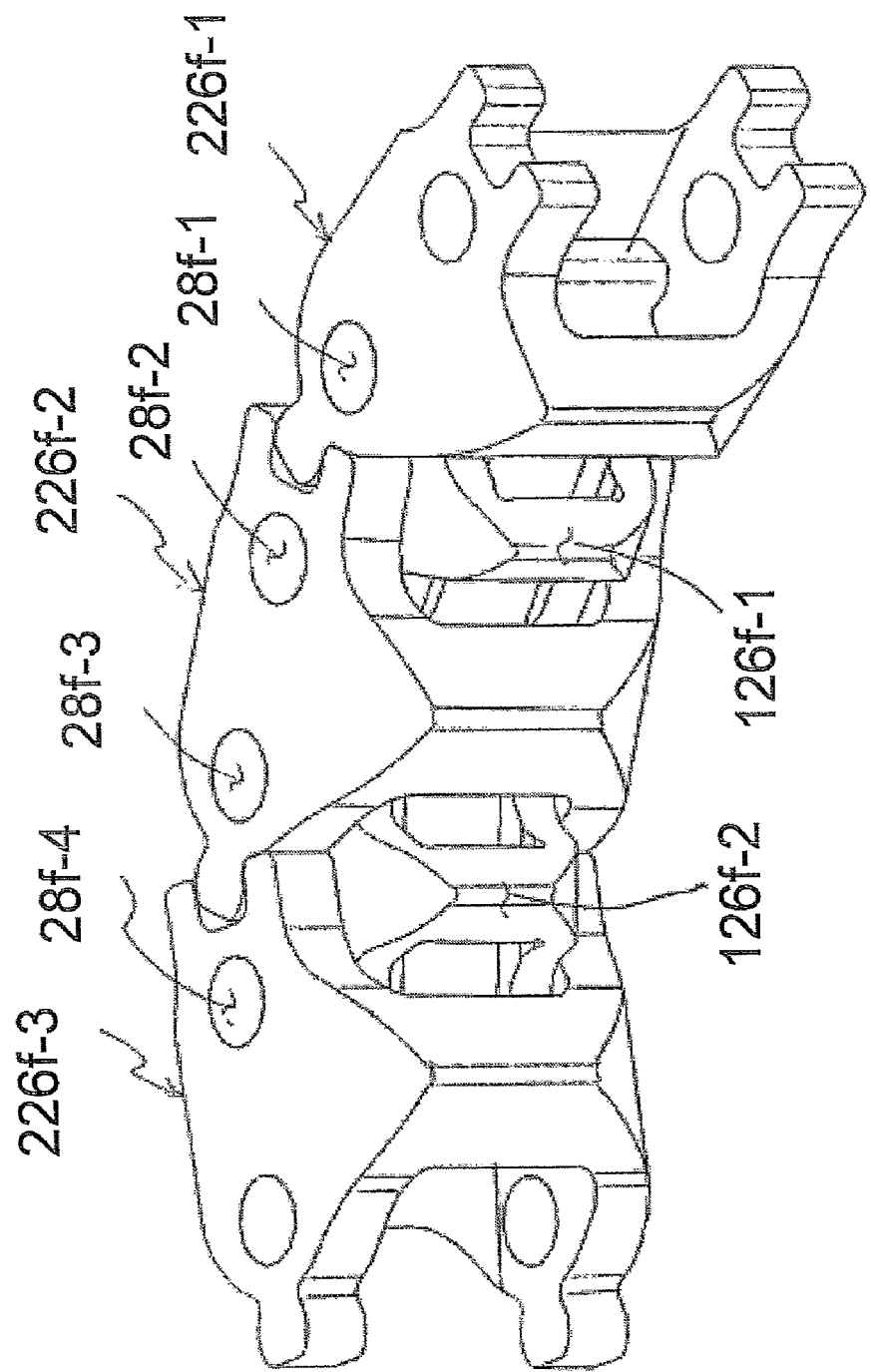

In accordance with this embodiment of the invention, if one outer link 226f is rotated relative to one inner link 126f, then the rest of the chain is also forced to rotate in a similar fashion. For instance, as shown in FIG. 34, outer link #2 (226f-2) is rotated relative to outer link #1 (226f-1), which forces inner link #1 (126f-1) to co-rotate since it is constrained by pin #1 (28f-1) and pin #2 (28f-2), which are also attached to outer link #1 (226f-1) and outer link #2 (226f-2) respectively.

Because the rotation of outer link #2 (226f-2) is greater than that of inner link #1 (126f-1), inner link #2 (126f-2) must rotate to keep an equidistant spacing between the two adjacent pins (28f-2 and 28f-3) of inner link #1 (126f-1) and inner link #2 (126f-2). In order for inner link #2 (126f-2) to rotate while the two adjacent pins (28f-3 and 28f-4) stay equidistant, outer link #3 (226f-3) must rotate relative to outer link #2 (226f-2), and so on, for the length of the chain.

Those skilled in the art will recognize that, the relative sizes of the inner links 126f and the outer links 226f may be varied in the design. For example, when the inner links 126f are sufficiently small in size, a clearance between the inner link side wall 175 and the outer link side wall 294 may define a passageway. In addition, an aperture (not shown) may be formed longitudinally across the inner links 126f, which together with a pin having an aperture (such as the pin 64 shown in FIG. 5) may form an inner passageway similar to that of the first embodiment discussed earlier.

In all of the foregoing embodiments, the articulating shafts may be covered with a flexible sheath.

It will be appreciated that a method is provided for articulating a shaft of a medical device. In FIGS. 1, 10 and 11, the method comprises providing pivot members 26 each having a single opening 51, extending a first slat assembly 31 through the single opening 51 of each pivot member 26, extending a second slat assembly 33 through the single opening 51 of each pivot member 26, pushing one of the first and second slat assemblies 31, 33 while concurrently pulling the other of the first and second slat assemblies 31, 33 to cause the pivot members 26 to collectively form a bend.

The method further comprises providing pins 28 each having a single pin aperture 64, and disposing the pins 28 adjacent to the pivot members 26 in an alternating configuration. The step of pushing one of the first and second slat assemblies 31, 33 while concurrently pulling the other of the first and second slat assemblies 31, 33 comprises moving an articulator 37 with a single finger, preferably a thumb. The step of moving the articulator 37 with the single finger comprises moving the articulator 37 to a left direction to cause the pivot members 26 to collectively form a bend in a first direction, and moving the articulator 37 to the right direction to cause the pivot members 26 to collectively form a bend to in a second direction.

The method further comprises actuating an end operating, or tool, assembly coupled distally to the articulating shaft 20b.

In all of the foregoing embodiments, it will be appreciated that the dual slat assemblies provide sufficient rigidity to the articulating shaft, especially when the articulating shaft is bent.

It will be appreciated that a method is also provided for assembling a shaft of a medical device. In FIGS. 25-34, the method comprises providing a plurality of inner link pivot members, providing a plurality of outer link pivot members, extending at least one of the inner link pivot members through an aperture of the outer link pivot members, connecting the at least one inner link pivot member with a neighboring outer link pivot member using a pin, and extending a first and a second slat assemblies through the aperture of each of the outer link pivot members such that pushing one of the first and second slat assemblies while concurrently pulling the other of the first and second slat assemblies causes the pivot members to collectively form a bend.

The method may further comprise engaging a female slot of an inner link pivot member with a male tab of a neighboring inner link pivot member, and engaging a female slot of an outer link pivot member with a male tab of a neighboring outer link pivot member.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A medical device, comprising:
   a bendable portion comprising a plurality of pivot members that are arranged in succession and a related plurality of pivot assemblies that pivotally connect adjacent ones of the plurality of pivot members;
   a first slat assembly extending along the bendable portion; and
   a second slat assembly extending along the bendable portion;
   wherein each of the first slat assembly and the second slat assembly is configured to push when the other of the first slat assembly and the second slat assembly pulls so as to cause the bendable portion to bend;
   wherein the pivot members comprise top and bottom plates and wherein adjacent ones of the plurality of pivot members are overlapped relative to one another;
   wherein the pivot assemblies comprise a plurality of pins and corresponding pin holes in the top and bottom plates of the pivot members, the pin holes of adjacent ones of the plurality of pivot members being aligned when the pivot members are overlapped relative to one another, the plurality of pins located within the aligned pin holes;
   wherein the pivot members comprise an alternating succession of inner and outer links, each of the inner and outer links defining an opening; and
   wherein each of the inner and outer inks comprises a male tab at one end and a female slot at an opposite end and wherein adjacent ones of the inner links are connected to one another by the male tab of one inner link and the female tab of the adjacent inner link and wherein adjacent ones of the outer links are connected to one another by the male tab of one outer link and the female tab of the adjacent outer link.

2. The device of claim 1 wherein the inner links and outer links are oriented such that their respective male tabs are extending in opposite directions.

3. The device of claim 1 wherein at least one of the male tabs of the inner links and the male tabs of the outer links comprises a tab neck having a predetermined shape and size and a slot opening having a predetermined shape and size adapted to restrict a relative movement between two adjacent links.

4. The device of claim 1 wherein the openings of the outer links and the openings of the inner links form a common passageway.

5. The device of claim 1 wherein each of the plurality of pins includes a pin aperture.

6. The device of claim 5, wherein:
the openings collectively define an outer passageway; and
the pin apertures collectively define an inner passageway.

7. The device of claim 6, wherein:
the first slat assembly extends through the outer passageway alongside a first side of the pins; and
the second slat assembly extends through the outer passageway alongside a second side of the pins opposite the first side of the pins.

8. The device of claim 1, further comprising an actuator extending through the bendable portion.

9. The device of claim 8, further comprising an operating mechanism coupled to the bendable portion, wherein the actuator is configured to actuate the operating mechanism.

10. The device of claim 1, further comprising a flexible tube extending through the bendable portion.

11. The device of claim 10, wherein the flexible tube comprises a passage for delivery of fluids.

12. The device of claim 1, further comprising an articulator coupled to the first slat assembly and the second slat assembly, wherein movement of the articulator causes one of the first and second slat assemblies to push and the other of the first and second slat assemblies to pull simultaneously.

13. The device of claim 12, wherein movement of the articulator in a first direction causes the bendable portion to bend in a second direction away from the first direction.

14. The device of claim 12, wherein movement of the articulator in a first direction causes the bendable portion to bend in a second direction toward the first direction.

15. The device of claim 1, wherein each pivot member defines a vertical axis, the device further comprising means for preventing each pin from moving vertically with respect to an adjacent pivot member.

16. The device of claim 1, wherein each pivot member has a laterally tapered thickness.

17. The device of claim 1, wherein:
the first slat assembly comprises a first plurality of layered slats; and
the second slat assembly comprises a second plurality of layered slats.

18. The device of claim 1, wherein:
the bendable portion is bendable in a first direction and an opposite second direction, the first and second directions collectively defining a range of motion;
the bendable portion comprises a preconfigured curve generally perpendicular to the range of motion.

19. The device of claim 18, wherein the first slat assembly and second slat assembly are curved in conformity with the preconfigured curve.

20. The device of claim 18, further comprising an actuator curved in conformity with the preconfigured curve.

21. The device of claim 18, wherein each pivot member has a tapered top portion.

22. The device of claim 18, wherein each pin has a tapered top portion.

23. The device of claim 5, further comprising an electrical wire extending through the pin apertures.

24. The device of claim 5, further comprising an optical fiber extending through the pin apertures.

* * * * *